(12) United States Patent
Bueno Calderon et al.

(10) Patent No.: US 7,629,365 B2
(45) Date of Patent: *Dec. 8, 2009

(54) HETEROCYCLIC COMPOUNDS

(75) Inventors: Jose Maria Bueno Calderon, Madrid (ES); Jesus Chicharro Gonzalo, Madrid (ES); M Pilar Manzano Chinchon, Madrid (ES)

(73) Assignee: Glaxo Group Limited, Brentford, Middlesex (GB)

( * ) Notice: Subject to any disclaimer, the term of this patent is extended or adjusted under 35 U.S.C. 154(b) by 0 days.

This patent is subject to a terminal disclaimer.

(21) Appl. No.: 11/755,849

(22) Filed: May 31, 2007

(65) Prior Publication Data

US 2007/0281977 A1    Dec. 6, 2007

(30) Foreign Application Priority Data

May 31, 2006  (EP) .................................. 06381025
Mar. 8, 2007  (EP) .................................. 07380072

(51) Int. Cl.
*A61K 31/4412*    (2006.01)
*A61P 33/02*      (2006.01)

(52) U.S. Cl. .................... 514/351; 514/345; 514/340; 514/344; 514/895; 546/290; 546/296; 546/300; 546/302

(58) Field of Classification Search ............... 514/351, 514/345, 340, 344, 895; 546/290, 296, 300, 546/302
See application file for complete search history.

(56) References Cited

U.S. PATENT DOCUMENTS 5,403,934 A * 4/1995 Batchelor et al. ........... 546/290

FOREIGN PATENT DOCUMENTS

| EP | 0447164 A | 9/1991 |
|---|---|---|
| WO | WO-9113873 A | 9/1991 |

OTHER PUBLICATIONS

Nitta et al, Mo(CO)n induced N-O bond cleavage of isoxazoles a convenient route to pyridin-4(1H) ones, Heterocycles, vol. 38, No. 4 1994.*
Patani et al , bioisosterism: A rational Approach in drug design, Chemical reviews, 1996, vol. 96, pp. 3147-3176.*

* cited by examiner

*Primary Examiner*—Ardin Marschel
*Assistant Examiner*—Savitha Rao
(74) *Attorney, Agent, or Firm*—Reid S. Willis; John Lemanowicz

(57) ABSTRACT

3-Chloro-6-(hydroxymethyl)-2-methyl-5-[4-({4-[(trifluoromethyl)oxy]phenyl}oxy)phenyl]-4(1H)-pyridinone, having the following formula:

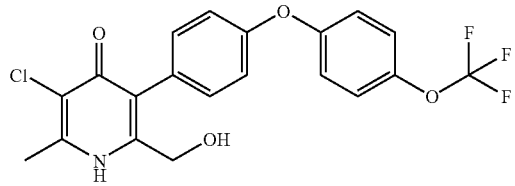

is described along with its pharmaceutically acceptable salts, processes for its preparation, pharmaceutical formulations thereof and its uses in treatment of certain parasitic infections such as malaria.

10 Claims, No Drawings

HETEROCYCLIC COMPOUNDS

FIELD OF THE INVENTION

The invention relates to heterocyclic compounds and their use in chemotherapy. More specifically, this invention is concerned with certain 4-pyridone (4-pyridinone) derivatives, processes for their preparation, pharmaceutical formulations thereof and their use in chemotherapy of certain parasitic infections such as malaria, and in particular infection by *Plasmodium falciparum*.

BACKGROUND OF THE INVENTION

Parasitic protozoal infections are responsible for a wide variety of diseases of medical and veterinary importance, including malaria in man and various coccidioses in birds, fish and mammals. Many of the diseases are life-threatening to the host and cause considerable economic loss in animal husbandry, such as species of *Eimeria, Theileria, Babesia, Cryptosporidium, Toxoplasma* (such as *Toxoplasma brucei*, African sleeping sickness and *Toxoplasma cruzi*, Chagas disease) and *Plasmodium* (such as *Plasmodium falciparum*), and the Mastigophora such as species of *Leishmania* (such as *Leishmania donovani*). Another parasitic organism of increasing concern is *Pneumocytis carinii*, which can cause an often fatal pneumonia in immunodeficient or immunocompromised hosts, including those infected with HIV.

Malaria is one of the major disease problems of the developing world. The most virulent malaria-causing parasite in humans is the parasite *Plasmodium falciparum*, which is the cause of hundreds of millions of cases of malaria per annum, and is thought to cause over 1 million deaths each year, Breman, J. G., et al., (2001) Am. Trop. Med. Hyg. 64, 1-11. One problem encountered in the treatment of malaria is the build-up of resistance by the parasite to available drugs. Thus, there is a need to develop new antimalarial drugs.

A group of 3,5-dihalo-2,6-dialkyl-4-pyridinol derivatives (the tautomeric form of 4-pyridones) is described in U.S. Pat. No. 3,206,358 as having anticoccidial activity.

European Patent Application No. 123239 discloses combinations of the aforementioned 4-pyridinol derivatives with antiprotozoal naphthoquinones, e.g. antimalarial naphthoquinones, in a potentiating ratio.

PCT Patent Application No. WO 91/13873 A1 discloses a class of 4-pyridone derivatives which exhibit activity against protozoa, in particular against the malarial parasite *Plasmodium falciparum*, and species of *Eimeria* as well as the parasitic organism *Pneumocytis carinii*. It has been found that compounds according to the present invention, generically disclosed in WO 91/13873 A1, and having a specific substitution pattern, exhibit improved properties over those compounds specifically disclosed in WO 91/13873 A1.

SUMMARY OF THE INVENTION

This invention is directed to certain 4-pyridone derivatives, processes for their preparation, pharmaceutical compositions comprising such compounds and use of the compounds in the chemotherapy of certain parasitic infections such as malaria, and in particular infection by *Plasmodium falciparum*.

DETAILED DESCRIPTION OF THE INVENTION

The present invention provides a compound of Formula I:

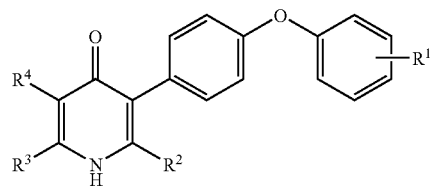

Wherein:
$R^1$ represents halo, $CF_3$ or $OCF_3$;
$R^4$ represents halo;
One of $R^2$ and $R^3$ represents methyl and the other represents
    —$(CH_2)_n$OH or —HC=N—$OR^5$;
$R^5$ represents H or —$C_1$-$C_4$alkyl;
n represents 1-4;

or a pharmaceutically acceptable derivative thereof.

Terms and Definitions

As used herein, the term "alkyl" as a group or a part of a group refers to a linear or branched saturated hydrocarbon group, containing the number of carbon atoms as specified; examples of such groups include methyl, ethyl, propyl, isopropyl, n-butyl, sec-butyl, isobutyl and tert-butyl and the like.

As used herein, "halo" refers to an fluoro, chloro, bromo or iodo group.

All aspects and embodiments of the invention described herein are in respect of compounds of Formula I, unless otherwise specified.

$R^1$ represents a substituent at any position of the phenyl ring. In one aspect of the invention $R^1$ represents a substituent at the meta or the para position of the phenyl ring. In another aspect of the invention $R^1$ represents a substituent at the para position of the phenyl ring.

In one aspect of the invention $R^1$ represents Br, Cl, F, $CF_3$ or $OCF_3$. In another aspect of the invention $R^1$ represents Cl, F, $CF_3$ or $OCF_3$. In a further aspect of the invention $R^1$ represents $CF_3$ or $OCF_3$. In a yet further aspect of the invention $R^1$ represents $OCF_3$.

In one aspect of the invention $R^4$ represents Br or Cl. In another aspect of the invention $R^4$ represents Cl.

In one aspect of the invention one of $R^2$ and $R^3$ represents methyl and the other represents —$(CH_2)_n$OH; in another aspect one of $R^2$ and $R^3$ represents methyl and the other represents —HC=N—$OR^5$.

In one aspect of the invention $R^2$ represents methyl and $R^3$ represents —$(CH_2)_n$OH or —HC=N—$OR^5$. In another aspect of the invention $R^2$ represents methyl and $R^3$ represents —$(CH_2)_n$OH.

In one aspect of the invention $R^3$ represents methyl and $R^2$ represents —$(CH_2)_n$OH or —HC=N—$OR^5$. In another aspect of the invention $R^3$ represents methyl and $R^2$ represents —$(CH_2)_n$OH.

In one aspect of the invention $R^5$ represents H or methyl.

In one aspect of the invention n represents 1 or 3. In a further aspect of the invention n represents 1.

The meaning of any functional group or substituent thereon at any one occurrence in Formula I, or any subformula thereof, is independent of its meaning, or any other functional group's or substituent's meaning, at any other occurrence, unless stated otherwise. It is to be understood that the present invention covers all combinations of the groups according to different aspects of the invention as described hereinabove.

In one aspect of the invention there is provided a compound, or a pharmaceutically acceptable derivative thereof, wherein the compound is selected from the group consisting of:

3-Chloro-6-(hydroxymethyl)-2-methyl-5-[4-({4-[(trifluoromethyl)oxy]phenyl}oxy)phenyl]-4(1H)-pyridinone;

3-Chloro-6-(hydroxymethyl)-2-methyl-5-[4-({4-[(trifluoromethyl)oxy]phenyl}oxy)phenyl]-4(1H)-pyridinone;

3-chloro-2-(hydroxymethyl)-6-methyl-5-[4-({4-[(trifluoromethyl)oxy]phenyl}oxy)phenyl]-4(1H)-pyridinone;

3-chloro-2-(hydroxymethyl)-6-methyl-5-(4-{[3-(trifluoromethyl)phenyl]oxy}phenyl)-4(1H)-pyridinone;

5-Chloro-6-methyl-4-oxo-3-[4-({4-[(trifluoromethyl)oxy]phenyl}oxy)phenyl]-1,4-dihydro-2-pyridinecarbaldehyde oxime;

5-Chloro-6-methyl-4-oxo-3-[4-({4-[(trifluoromethyl)oxy]phenyl}oxy)phenyl]-1,4-dihydro-2-pyridinecarbaldehyde-O-methyloxime;

3-chloro-6-methyl-4-oxo-5-[4-({4-[(trifluoromethyl)oxy]phenyl}oxy)phenyl]-1,4-dihydro-2-pyridinecarbaldehyde oxime; and 3-chloro-6-(3-hydroxypropyl)-2-methyl-5-[4-({4-[(trifluoromethyl)oxy]phenyl}oxy)phenyl]-4(1H)-pyridinone.

As used herein, the term "pharmaceutically acceptable derivative", means any pharmaceutically acceptable salt, solvate, or prodrug e.g. ester or carbamate of a compound of Formula I, which upon administration to the recipient is capable of providing (directly or indirectly) a compound of Formula I, or an active metabolite or residue thereof. Such derivatives are recognizable to those skilled in the art, without undue experimentation. Nevertheless, reference is made to the teaching of Burger's Medicinal Chemistry and Drug Discovery, 5th Edition, Vol 1: Principles and Practice, which is incorporated herein by reference to the extent of teaching such derivatives. In one aspect of the invention pharmaceutically acceptable derivatives are salts, solvates, esters and carbamates. In another aspect of the invention pharmaceutically acceptable derivatives are salts, solvates and esters. In a further aspect, pharmaceutically acceptable derivatives are salts and solvates. In a yet further aspect, pharmaceutically acceptable derivatives are salts. In one aspect, pharmaceutically acceptable derivatives at the nitrogen of the pyridinone ring include —$OC_{1-6}$alkyl and —$O(CO)C_{1-6}$alkyl. In another aspect, when $R^2$ or $R^3$ are —$(CH_2)_n$OH, pharmaceutically acceptable derivatives of the OH group of $R^2$ or $R^3$ include —$O(CO)C_{1-6}$alkyl (for example —$O(CO)CH_3$) and —$O(CO)N(C_{1-4}alkyl)$-$C_{1-2}$alkyl-$N^+H_2(C_{1-6}alkyl)$. In a further aspect, pharmaceutically acceptable derivatives at the hydroxy group of the 4-pyridinol tautomeric form include —$O(CO)C_{1-6}$alkyl (for example —$O(CO)CH_3$) and —$O(CO)N(C_{1-4}alkyl)$-$C_{1-2}$alkyl-$N^+H_2(C_{1-6}alkyl)$.

An ester of a compound of Formula I may be hydrolysable under in vivo conditions in the human body. Suitable pharmaceutically acceptable in vivo hydrolysable ester groups include those which break down readily in the human body to leave the parent acid or the salt thereof. An ester may be formed at a hydroxy group (OH) of a compound of Formula I using methods well known in the art involving reaction with the corresponding acid. For example, esters may be $C_{1-6}$alkyl esters, wherein alkyl is as defined herein, e.g. methyl esters, ethyl esters and the like.

It will be appreciated that certain pharmaceutically acceptable salts of the compounds according to Formula I may be prepared, since the compounds of the invention are weakly amphoteric. Indeed, in certain embodiments of the invention, pharmaceutically acceptable salts of the compounds according to Formula I may be preferred over the respective free base or free acid because such salts impart greater stability or solubility to the molecule thereby facilitating formulation into a dosage form. The compounds of the present invention may also be administered as a pharmaceutically acceptable salt. Accordingly, the invention is further directed to pharmaceutically acceptable salts of the compounds according to Formula I.

As used herein, the term "pharmaceutically acceptable salts" refers to salts that retain the desired biological activity of the subject compound and exhibit minimal undesired toxicological effects. For a review on suitable salts see Berge et al, J. Pharm. Sci., 1977, 66, 1-19. The term "pharmaceutically acceptable salts" includes both pharmaceutically acceptable acid addition salts and pharmaceutically acceptable base addition salts. These pharmaceutically acceptable salts may be prepared in situ during the final isolation and purification of the compound, or by separately reacting the purified compound in its free acid or free base form with a suitable base or acid, respectively. The salt may precipitate from solution and be collected by filtration or may be recovered by evaporation of the solvent.

In certain embodiments, compounds according to Formula I may contain an acidic functional group and may therefore be capable of forming pharmaceutically acceptable base addition salts by treatment with a suitable base. A pharmaceutically acceptable base addition salt may be formed by reaction of a compound of Formula I with a suitable strong inorganic base, optionally in a suitable solvent such as an organic solvent, to give the base addition salt which may be isolated for example by crystallisation and filtration. Pharmaceutically acceptable base salts include include pharmaceutically acceptable metal salts, for example pharmaceutically acceptable alkali-metal or alkaline-earth-metal salts such as hydroxides, sodium, potassium, lithium.

In certain embodiments, compounds according to Formula I may contain a basic functional group and may therefore be capable of forming pharmaceutically acceptable acid addition salts by treatment with a suitable acid. A pharmaceutically acceptable acid addition salt may be formed by reaction of a compound of Formula I with a suitable strong inorganic or organic acid (such as hydrobromic, hydrochloric, sulfuric, nitric, phosphoric, perchloric, p-toluenesulfonic, benzenesulfonic, methanesulfonic, ethanesulfonic, 2-hydroxyethanesulfonic, naphthalenesulfonic (e.g. 2-naphthalenesulfonic), optionally in a suitable solvent such as an organic solvent, to give the salt which is usually isolated for example by crystallisation and filtration. Pharmaceutically acceptable acid addition salts include a hydrobromide, hydrochloride, hydroiodide, sulfate, bisulfate, nitrate, phosphate, perchlorate, p-toluenesulfonate, benzenesulfonate, methanesulfonate, ethanesulfonate, 2-hydroxyethanesulfonate or naphthalenesulfonate (e.g. 2-naphthalenesulfonate) salt. In one embodiment, a pharmaceutically acceptable acid addition salt of a compound of Formula I is a salt of a strong acid, for example a hydrobromide, hydrochloride, hydroiodide, sulfate, nitrate, perchlorate, phosphate p-toluenesulfonic, benzenesulfonic, methanesulfonic salt.

The invention includes within its scope all possible stoichiometric and non-stoichiometric forms of the salts of the compounds of Formula I.

As used herein, the term "compounds of the invention" means the compounds according to Formula I and the pharmaceutically acceptable derivatives thereof. The term "a compound of the invention" means any one of the compounds of the invention as defined above.

The compounds of the invention may exist as solids or liquids, both of which are included in the invention. In the solid state, the compounds of the invention may exist as either amorphous material or in crystalline form, or as a mixture thereof. It will be appreciated that pharmaceutically acceptable solvates of compounds of the invention may be formed wherein solvent molecules are incorporated into the crystalline lattice during crystallisation. Solvates may involve non-aqueous solvents such as ethanol, isopropanol, dimethylsulfoxide (DMSO), acetic acid, ethanolamine, and ethyl acetate, or they may involve water as the solvent that is incorporated into the crystalline lattice. Solvates wherein water is the solvent that is incorporated into the crystalline lattice are typically referred to as "hydrates." The invention includes all such solvates.

It will be appreciated that compounds of the invention can exist in different tautomeric forms. In particular, compounds of Formula I may exist in the 4-pyridinol tautomeric form as follows:

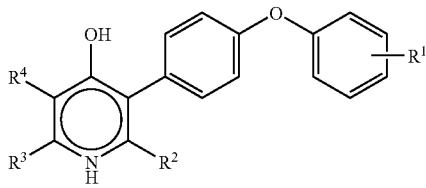

All possible tautomeric forms of the compounds of Formula I are contemplated to be within the scope of the present invention. In one aspect of the invention there is provided compounds of Formula I in the 4-pyridone tautomeric form. In another aspect of the invention there is provided compounds of Formula I in the 4-pyridinol tautomeric form. In a further aspect of the invention there is provided a mixture of compounds of Formula I in the 4-pyridone and 4-pyridinol tautomeric forms. In a yet further aspect of the invention, the mixture of 4-pyridone and 4-pyridinol tautomeric forms of compounds of Formula I is an equilibrium mixture.

It will further be appreciated that compounds of the invention which contain a double bond, for example an oxime double bond, may be present as a mixture of E and Z isomers with respect to the geometry about the double bond. The mixture may contain E and Z isomers in equal amounts, or the mixture may contain an excess of either Z or E isomer. Compounds of the invention may alternatively be present in their respective pure E and Z geometric isomeric form about each double bond.

It will also be appreciated that compounds of the invention which exist as polymorphs, enantiomers and mixtures thereof are all contemplated to be within the scope of the present invention.

Certain compounds of the invention may have an improved pharmacokinetic profile (e.g. they may be more orally bioavailable, or they may display improved oral exposure).

According to another aspect of the invention there is provided a compound of Formula I or a pharmaceutically acceptable derivative thereof for use in human or veterinary medical therapy.

The compounds of the invention can be useful in the treatment of certain parasitic infections such as parasitic protozoal infections by the malarial parasite *Plasmodium falciparum*, species of *Eimeria, Pneumocytis carni, Trypanosoma cruzi,* *Trypanosoma brucei* or *Leishmania donovani*. In particular, the compounds of the invention can be useful for treatment of infection by *Plasmodium falciparum*. Accordingly, the invention is directed to methods of treating such conditions.

In one aspect of the invention, there is provided a compound of Formula I or a pharmaceutically acceptable derivative thereof, for use in therapy, for example the treatment of parasitic protozoal infections such as malaria, for example infection by *Plasmodium falciparum*.

In another aspect of the invention there is provided the use of a compound of Formula I or a pharmaceutically acceptable derivative thereof in the manufacture of a medicament for the treatment of parasitic protozoal infections such as malaria, for example a condition caused by infection by *Plasmodium falciparum*.

In another aspect of the invention there is provided a method for the treatment of a human or animal subject suffering from a parasitic protozoal infection such as malaria, for example infection by *Plasmodium falciparum*, comprising administering to said human or animal subject an effective amount of a compound of Formula I or a pharmaceutically acceptable derivative thereof, or a pharmaceutical composition comprising a compound of Formula I or a pharmaceutically acceptable derivative thereof.

The methods of treatment of the invention comprise administering a safe and effective amount of a compound according to Formula I or a pharmaceutically acceptable derivative thereof to a patient in need thereof.

As used herein, "treatment" means: (1) the amelioration or prevention of the condition being treated or one or more of the biological manifestations of the condition being treated, (2) the interference with (a) one or more points in the biological cascade that leads to or is responsible for the condition being treated or (b) one or more of the biological manifestations of the condition being treated, or (3) the alleviation of one or more of the symptoms or effects associated with the condition being treated. The skilled artisan will appreciate that "prevention" is not an absolute term. In medicine, "prevention" is understood to refer to the prophylactic administration of a drug to substantially diminish the likelihood or severity of a condition or biological manifestation thereof, or to delay the onset of such condition or biological manifestation thereof.

As used herein, "safe and effective amount" means an amount of the compound sufficient to significantly induce a positive modification in the condition to be treated but low enough to avoid serious side effects (at a reasonable benefit/risk ratio) within the scope of sound medical judgment. A safe and effective amount of a compound of the invention will vary with the particular compound chosen (e.g. depending on the potency, efficacy, and half-life of the compound); the route of administration chosen; the nature of the infection and/or condition being treated; the severity of the infection and/or condition being treated; the age, size, weight, and physical condition of the patient being treated; the medical history of the patient to be treated; the duration of the treatment; the nature of concurrent therapy; the desired therapeutic effect; and like factors, but can nevertheless be routinely determined by the skilled artisan.

As used herein, "patient" refers to a human or other animal.

The compounds of the invention may be administered by any suitable route of administration, including systemic administration. Systemic administration includes oral administration, parenteral administration, transdermal administration, rectal administration, and administration by inhalation. Parenteral administration refers to routes of administration other than enteral, transdermal, or by inhalation, and is typically by injection or infusion. Parenteral administration includes intravenous, intramuscular, and subcutaneous injection or infusion. Inhalation refers to administration into the patient's lungs whether inhaled through the mouth or through the nasal passages. Topical administration includes dermal application to the skin as well as intraocular, buccal (e.g. sub-lingually), rectal, intravaginal, and intranasal administration.

The compounds of the invention may be administered once only, or according to a dosing regimen wherein a number of doses are administered at varying intervals of time for a given period of time. For example, doses may be administered one, two, three, or four times per day. Doses may be administered until the desired therapeutic effect is achieved or indefinitely to maintain the desired therapeutic effect. The dosage will also vary according to the nature of the intended treatment, wherein "treatment" is as hereinbelow defined, for example a greater dose of compound may be given for amelioration as compared with prevention of a condition being treated. Suitable dosing regimens for a compound of the invention depend on the pharmacokinetic properties of that compound, such as absorption, distribution, and half-life, which can be determined by the skilled artisan. In addition, suitable dosing regimens for a compound of the invention, including the duration such regimens are administered, depend on the route of administration of the compound, on the condition being treated, the severity of the condition being treated, the age and physical condition of the patient being treated, the medical history of the patient to be treated, the nature of any concurrent therapy, the desired therapeutic effect, and like factors within the knowledge and expertise of the skilled artisan. It will be further understood by such skilled artisans that suitable dosing regimens may require adjustment given an individual patient's response to the dosing regimen or over time as individual patient needs change. It will also be appreciated that if the compounds of the present invention are administered in combination with one or more additional active therapeutic agents as discussed further hereinbelow, the dosing regimen of the compounds of the invention may also vary according to the nature and amount of the one or more additional active therapeutic agents as necessary.

Typical daily dosages may vary depending upon the particular route of administration chosen. Typical daily dosages for oral administration range from about 0.01 to about 25 mg/kg, in one embodiment from about 0.1 to about 14 mg/kg. Typical daily dosages for parenteral administration range from about 0.001 to about 10 mg/kg; in one embodiment from about 0.01 to about 6 mg/kg. In one embodiment, the daily dose range of the compounds is from 100-1000 mg per day.

The compounds of Formula I may also be used in combination with other active therapeutic agents. The invention thus provides, in a further aspect, a combination comprising a compound of Formula I or a pharmaceutically acceptable derivative thereof together with a further active therapeutic agent. When a compound of Formula I or a pharmaceutically acceptable derivative thereof is used in combination with a second active therapeutic agent which is active against the same disease state the dose of each compound may differ from that when the compound is used alone. Appropriate doses will be readily appreciated by those skilled in the art. It will be appreciated that the amount of a compound of the invention required for use in treatment will vary with the nature of the condition being treated and the age and condition of the patient and will be ultimately at the discretion of the attendant physician or veterinarian.

The compounds of the present invention may be used alone or in combination with one or more additional active therapeutic agents, such as other antiparasitic drugs, for example antimalarial drugs.

Such other active therapeutic agents include antimalarial drugs, such as folates (e.g. chloroquine, mefloquine, primaquine pyrimethamine, quinine, artemisinin, halofantrine, doxycycline, amodiquine, atovaquone, tafenoquine) and antifolates (e.g. dapsone, proguanil, sulfadoxine, pyrimethamine, chlorcycloguanil, cycloguanil).

The combinations referred to above may conveniently be presented for use in the form of a pharmaceutical formulation and thus pharmaceutical formulations comprising a combination as defined above together with a pharmaceutically acceptable carrier and/or excipient comprise a further aspect of the invention. The individual components of such combinations may be administered either sequentially or simultaneously in separate or combined pharmaceutical formulations by any convenient route.

When administration is sequential, either the compound of the present invention or the one or more additional active therapeutic agent(s) may be administered first. When administration is simultaneous, the combination may be administered either in the same or different pharmaceutical composition. When combined in the same formulation it will be appreciated that the compound of the present invention and the one or more additional active therapeutic agent(s) must be stable and compatible with each other and the other components of the formulation. When formulated separately the compound of the present invention and the one or more additional active therapeutic agent(s) may be provided in any convenient formulation, conveniently in such manner as are known for such compounds in the art.

Compositions

The compounds of the invention will normally, but not necessarily, be formulated into pharmaceutical compositions prior to administration to a patient. In one aspect, the invention is directed to pharmaceutical compositions comprising a compound of the invention. In another aspect the invention is directed to a pharmaceutical composition comprising a compound of the invention and one or more pharmaceutically acceptable carriers and/or excipients.

The carrier and/or excipient must be "acceptable" in the sense of being compatible with the other ingredients of the formulation and not deleterious to the receipient thereof.

The pharmaceutical compositions of the invention may be prepared and packaged in bulk form wherein a safe and effective amount of a compound of the invention can be extracted and then given to the patient such as with powders or syrups. Alternatively, the pharmaceutical compositions of the invention may be prepared and packaged in unit dosage form wherein each physically discrete unit contains a safe and effective amount of a compound of the invention. When prepared in unit dosage form, the pharmaceutical compositions of the invention typically contain from about 0.1 to 100 mg, in another aspect 0.1 mg to about 50 mg of a compound of the invention.

The pharmaceutical compositions of the invention typically contain one compound of the invention. However, in certain embodiments, the pharmaceutical compositions of the invention contain more than one compound of the invention. For example, in certain embodiments the pharmaceutical compositions of the invention contain two compounds of the invention. In addition, the pharmaceutical compositions of the invention may optionally further comprise one or more additional active therapeutic compounds. The pharmaceutical compositions of the invention typically contain more than one pharmaceutically acceptable excipient. However, in certain embodiments, the pharmaceutical compositions of the invention contain one pharmaceutically acceptable excipient.

As used herein, the term "pharmaceutically acceptable" means suitable for pharmaceutical use.

The compound of the invention and the pharmaceutically acceptable excipient or excipients will typically be formulated into a dosage form adapted for administration to the patient by the desired route of administration. For example, dosage forms include those adapted for (1) oral administration such as tablets, capsules, caplets, pills, troches, powders, syrups, elixers, suspensions, solutions, emulsions, sachets, and cachets; (2) parenteral administration such as sterile solutions, suspensions, and powders for reconstitution; (3) transdermal administration such as transdermal patches; (4) rectal administration such as suppositories; (5) inhalation such as aerosols and solutions; and (6) topical administration such as creams, ointments, lotions, solutions, pastes, sprays, foams, and gels.

Suitable pharmaceutically acceptable excipients will vary depending upon the particular dosage form chosen. In addition, suitable pharmaceutically acceptable excipients may be chosen for a particular function that they may serve in the composition. For example, certain pharmaceutically acceptable excipients may be chosen for their ability to facilitate the production of uniform dosage forms. Certain pharmaceutically acceptable excipients may be chosen for their ability to facilitate the production of stable dosage forms. Certain pharmaceutically acceptable excipients may be chosen for their ability to facilitate the carriage or transport of the compound or compounds of the invention from one organ, or portion of the body, to another organ, or portion of the body, once administered to the patient. Certain pharmaceutically acceptable excipients may be chosen for their ability to enhance patient compliance.

Suitable pharmaceutically acceptable excipients include the following types of excipients: binders, disintegrants, lubricants, glidants, granulating agents, coating agents, wetting agents, solvents, co-solvents, suspending agents, emulsifiers, sweeteners, flavouring agents, flavour masking agents, coloring agents, anticaking agents, humectants, chelating agents, plasticizers, viscosity increasing agents, antioxidants, preservatives, stabilizers, surfactants, and buffering agents. The skilled artisan will appreciate that certain pharmaceutically acceptable excipients may serve more than one function and may serve alternative functions depending on how much of the excipient is present in the formulation and what other ingredients are present in the formulation.

Skilled artisans possess the knowledge and skill in the art to enable them to select suitable pharmaceutically acceptable excipients in appropriate amounts for use in the invention. In addition, there are a number of resources that are available to the skilled artisan which describe pharmaceutically acceptable excipients and may be useful in selecting suitable pharmaceutically acceptable excipients. Examples include Remington's Pharmaceutical Sciences (Mack Publishing Company), The Handbook of Pharmaceutical Additives (Gower Publishing Limited), and The Handbook of Pharmaceutical Excipients (the American Pharmaceutical Association and the Pharmaceutical Press).

The pharmaceutical compositions of the invention are prepared using techniques and methods known to those skilled in the art. Some of the methods commonly used in the art are described in Remington's Pharmaceutical Sciences (Mack Publishing Company).

In one aspect, the invention is directed to a solid or liquid oral dosage form such as a liquid, tablet, lozenge or a capsule, comprising a safe and effective amount of a compound of the invention and a carrier. The carrier may be in the form of a diluent or filler. Suitable diluents and fillers in general include lactose, sucrose, dextrose, mannitol, sorbitol, starch (e.g. corn starch, potato starch, and pre-gelatinized starch), cellulose and its derivatives (e.g. microcrystalline cellulose), calcium sulfate, and dibasic calcium phosphate. A liquid dosage form will generally consist of a suspension or solution of the compound or pharmaceutically acceptable derivative in a liquid carrier for example, ethanol, olive oil, glycerine, glucose (syrup) or water (e.g. with an added flavouring, suspending, or colouring agent). Where the composition is in the form of a tablet or lozenge, any pharmaceutical carrier routinely used for preparing solid formulations may be used. Examples of such carriers include magnesium stearate, terra alba, talc, gelatin, acacia, stearic acid, starch, lactose and sucrose. Where the composition is in the form of a capsule, any routine encapsulation is suitable, for example using the aforementioned carriers or a semi solid e.g. mono di-glycerides of capric acid, Gelucire™ and Labrasol™, or a hard capsule shell e.g gelatin. Where the composition is in the form of a soft shell capsule e.g. gelatin, any pharmaceutical carrier routinely used for preparing dispersions or suspensions may be considered, for example aqueous gums or oils, and may be incorporated in a soft capsule shell.

An oral solid dosage form may further comprise an excipient in the form of a binder. Suitable binders include starch (e.g. corn starch, potato starch, and pre-gelatinized starch), gelatin, acacia, sodium alginate, alginic acid, tragacanth, guar gum, povidone, and cellulose and its derivatives (e.g. microcrystalline cellulose). The oral solid dosage form may further comprise an excipient in the form of a disintegrant. Suitable disintegrants include crospovidone, sodium starch glycolate, croscarmelose, alginic acid, and sodium carboxymethyl cellulose. The oral solid dosage form may further comprise an excipient in the form of a lubricant. Suitable lubricants include stearic acid, magnesium stearate, calcium stearate, and talc.

There is further provided by the present invention a process of preparing a pharmaceutical composition, which process comprises mixing at least one compound of Formula I or a pharmaceutically acceptable derivative thereof, together with a pharmaceutically acceptable carrier and/or excipient.

Preparations for oral administration may be suitably formulated to give controlled/extended release of the active compound.

Abbreviations

In describing the invention, chemical elements are identified in accordance with the Periodic Table of the Elements. Abbreviations and symbols utilised herein are in accordance with the common usage of such abbreviations and symbols by those skilled in the chemical arts. The following abbreviations are used herein:

| | |
|---|---|
| AcOEt, EtOAc | ethyl acetate |
| approx. | approximately |
| bar | $1 \times 10^5$ Pa (Pascal) |
| brine | saturated aqueous sodium chloride |
| n-BuLi | n-butyllithium |
| t-BuOMe | tert-butyl-methyl-ether |
| cat. ref. | catalogue reference |
| $CDCl_3$ | deuterated chloroform |
| $CD_3OD$ | deuterated methanol |

-continued

| | |
|---|---|
| conc. | concentrated |
| cpm | counts per minute (unit of radiactivity) |
| DCM | dichloromethane |
| DIBAH | diisobutyl aluminium hydride |
| DMF | N,N-dimethylformamide |
| DMSO | dimethylsulfoxide |
| DMSO-$d_6$ | deuterated dimethylsulfoxide |
| ES MS | Electrospray mass spectrometry |
| EtOH | ethanol |
| h | hour(s) |
| human sera AB | Serum obtained from human blood type AB |
| HEPES | 4-(2-Hydroxyethyl) piperazine-1-ethanesulfonic acid |
| HPLC | High Performance Liquid Chromatography |
| HT | Hypoxanthine |
| HT supplement | 0.15 mM hypoxanthine and 24 μM thymidine, (GIBCO ™ cat. ref.: 41065) |
| Incomplete blood donation | a volume of blood lower than 450 ml used for research |
| L | liter(s) |
| LDA | lithium diisopropylamide |
| MeOH | methanol |
| min. | minute(s) |
| NaTaurochol. | sodium Taurocholic |
| NBS | N-bromosuccinimide |
| NCS | N-chlorosuccinimide |
| NMP | N-methyl-pyrrolidinone |
| NMR | Nuclear Magnectic Resonance spectroscopy |
| Pa | Pascal (SI unit of pressure: $m^{-1} \cdot kg \cdot s^{-2}$) |
| PRBCs | parasitized red blood cells |
| pH | $-Log_{10}$ of the hydrogen ion concentration |
| RBCs | red blood cells |
| TBDMS | tert-butyldimethylsilyl |
| TBDPS | tert-butyldiphenylsilyl |
| TCCA | trichloroisocyanuric acid |
| TMHD | 2,2,6,6-tetramethyl-heptane-3,5-dione |
| RPMI | Roswell Park Memorial Institute medium* |
| THF | tetrahydrofuran |
| v/v | volume ratio |
| w/w | weight ratio, e.g. percentage by weight |

*(for details about this medium, see Divo, A. A. , et al., Nutritional requirements of Plasmodium falciparum in culture. I. Exogenously supplied dialyzable components necessary for continuous growth. J Protozool, 1985. 32(1): p. 59-64).

Compound Preparation

The general procedures used to synthesise the compounds of Formula I are described in reaction Schemes 1-24 and are illustrated in the Examples.

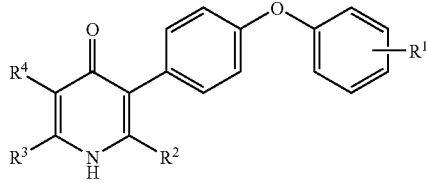

I

Throughout the specification, general Formulae are designated by Roman numerals I, II, III, IV etc. Subsets of compounds of Formula I are defined as Ia, Ib, Ic, Id and Ie; subsets of other Formulae are expressed in an analogous fashion.

Compounds of Formula Ia, which are compounds of Formula I wherein $R^1$ represents halo, $CF_3$ or $OCF_3$; $R^4$ represents halo; $R^2$ represents —$CH_2OH$; and $R^3$ represents methyl, may be prepared from compounds of Formula II, wherein $R^1$ represents halo, $CF_3$ or $OCF_3$, according to Scheme 1 by reaction of II with an appropriate halogenating agent such as a halosuccinimide (NBS, NCS), trichloroisocyanuric acid (TCCA) or bromine in a suitable solvent such as a mixture of dichloromethane and methanol.

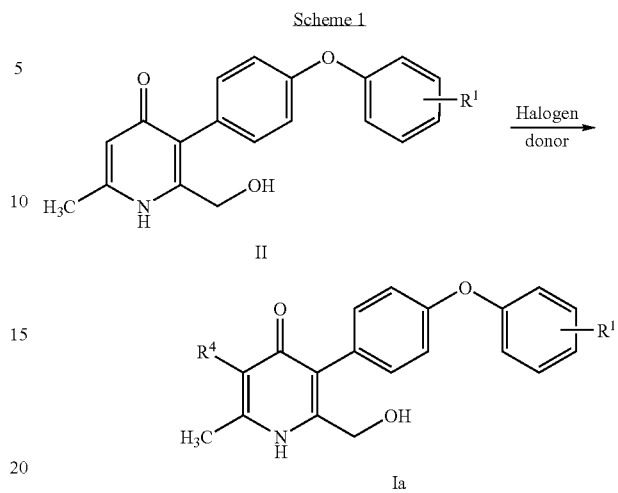

Compounds of Formula II may be prepared from compounds of Formula III, wherein $R^1$ represents fluoro, chloro, $CF_3$ or $OCF_3$ and PG is a sterically hindered hydroxy protecting group, for example TBDMS or TBDPS, according to Scheme 2, by aminolysis, with concurrent deprotection of the protecting group PG, for example in the presence of aqueous ammonia, suitably under pressure and elevated temperature, for example between 120° C. and 160° C., in a suitable solvent, such as EtOH or MeOH.

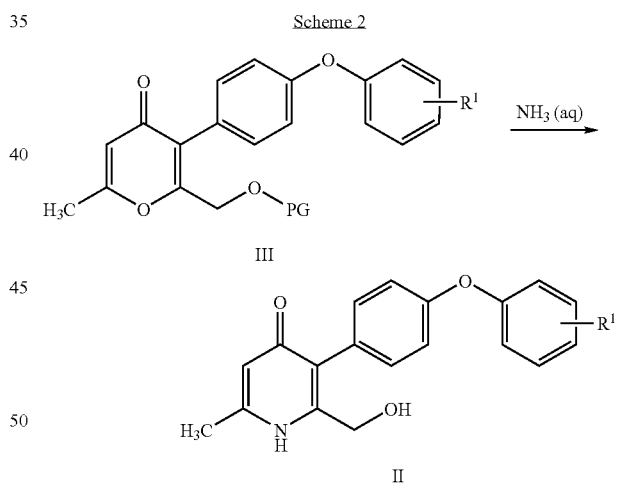

Compounds of Formula III may be prepared using a Suzuki cross-coupling reaction between compounds of Formula IV, wherein PG is as defined for Formula III, and boronic acid compounds of Formula V, wherein $R^1$ represents fluoro, chloro, $CF_3$ or $OCF_3$, according to Scheme 3. The compounds of Formula IV may be heated, for example at a temperature between 50° C. and 100° C., with V in an appropriate solvent such as toluene, ethanol, DMF or a mixture thereof, in the presence of a base such as sodium carbonate or potassium carbonate, and a suitable palladium catalyst. In one aspect, the palladium catalyst is Bis(triphenylphosphine)palladium (II)chloride.

Scheme 3

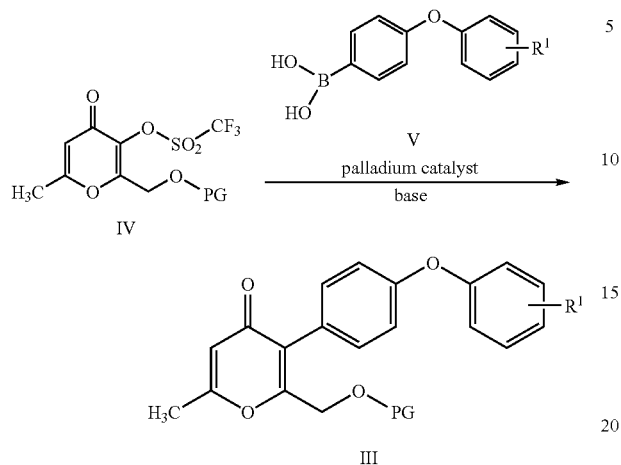

Compounds of Formula IV may be prepared from compounds of Formula VI, wherein PG is as defined for Formula III, according to Scheme 4 by treatment of VI with a mild trifluoromethanesulfonylating agent in a suitable solvent such as dimethylformamide in the presence of a suitable base such as sodium or potassium carbonate. In one aspect, the trifluoromethanesulfonylating agent is N-phenyl-trifluoromethanesulfonimide.

Scheme 4

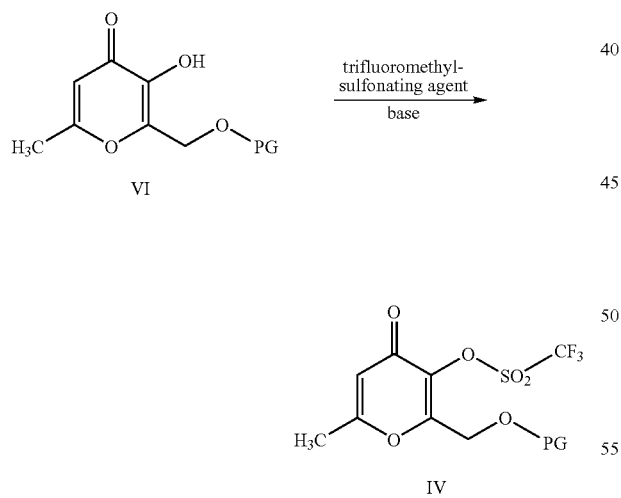

Compounds of Formula VI may be prepared from compounds of Formula VII, wherein PG is as defined for Formula III, and $PG_1$ is a different hydroxy protecting group from PG by a selective deprotection reaction of VII to remove $PG_1$, according to Scheme 5. For example, when $PG_1$ is benzyl, deprotection may be carried out using hydrogenation in the presence of a suitable catalyst, for example palladium on charcoal, in a suitable solvent such as ethyl acetate.

Scheme 5

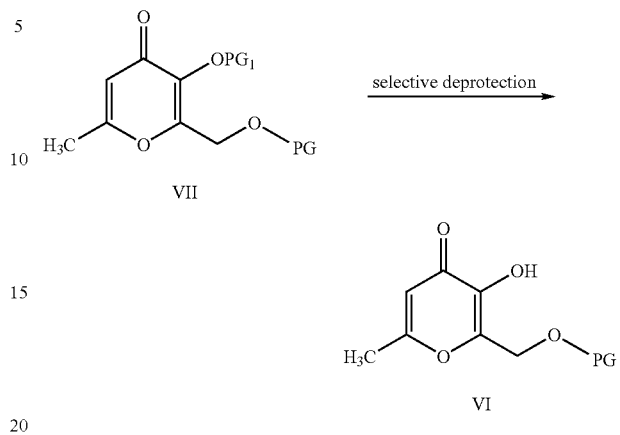

Compounds of Formula VII may be prepared from compounds of Formula VIII, wherein $PG_1$ is as defined for Formula VII, by a reaction to protect the hydroxy group of Formula VIII with a suitable protecting group PG, according to Scheme 6. For example, when the protecting group PG is TBDMS, the compound of Formula VIII may be treated with TBDMSCl in the presence of a base, e.g. imidazole, in a suitable solvent such as DMF.

Scheme 6

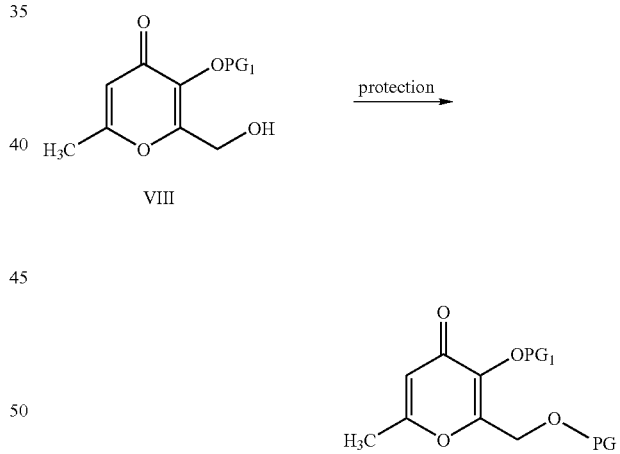

Compounds of Formula VIII may be prepared from the compound of Formula IX, according to Scheme 7. Compound IX may be treated with formaldehyde in the presence of a suitable base, such as aqueous sodium hydroxide, then the resulting intermediate product subjected to a protection reaction to introduce $PG_1$. For example, when $PG_1$ is benzyl, the intermediate product may be treated with benzyl chloride or benzyl bromide in the presence of a suitable catalyst, such as tetra-N-butylammonium bromide.

Scheme 7

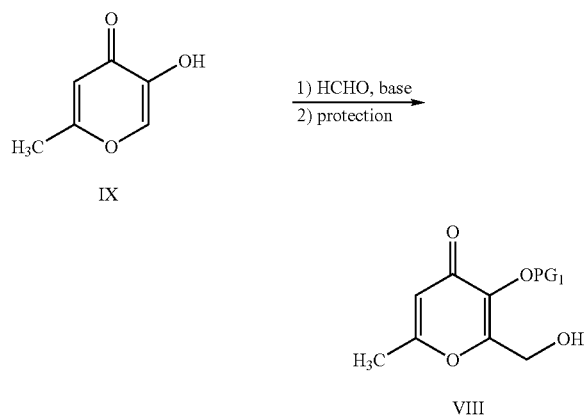

The compound of Formula IX may be prepared from the compound of Formula X according to Scheme 8 by reaction of IX with zinc in the presence of conc. HCl in a suitable solvent, such as water, at elevated temperature, for example between 50° C. and 90° C.

Scheme 8

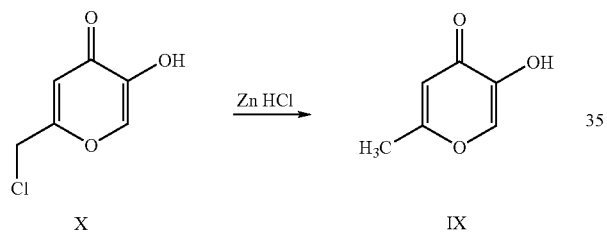

The compound of Formula X may be prepared from by reacting the compound of Formula XI with a chlorinating agent such as thionyl chloride ($SOCl_2$) or phosphoryl chloride ($POCl_3$) according to Scheme 9.

Scheme 9

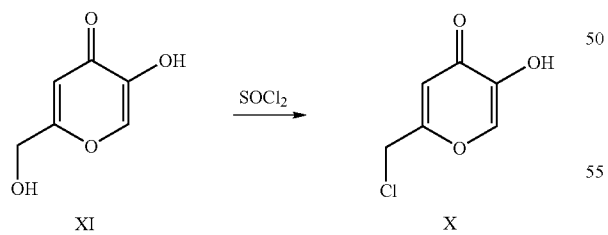

The boronic acids of Formula V may be prepared from compounds of Formula XII, wherein $R^1$ represents fluoro, chloro, $CF_3$ or $OCF_3$, according to Scheme 10, by treatment of XII with a suitable base such as n-BuLi in the presence of tri-isopropylborate in a suitable solvent such as THF, at between −60° C. and −78° C., followed by acid hydrolysis, for example with 6N HCl.

Scheme 10

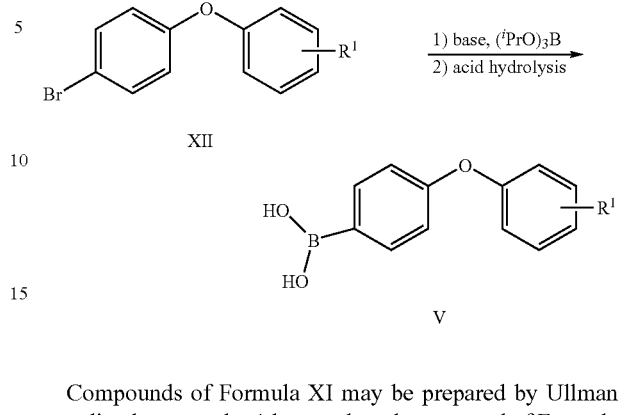

Compounds of Formula XI may be prepared by Ullman coupling between the 4-bromophenol compound of Formula XIII which is commercially available, and iodophenyl compounds of Formula XIV which are also commercially available, wherein $R^1$ represents fluoro, chloro, $CF_3$ or $OCF_3$, according to Scheme 11. Compound XIII may be reacted with XIV in the presence of a copper(I) salt such as copper(I) chloride and a base, such as caesium carbonate and an additive such as 2,2,6,6-tetramethyl-heptane-3,5-dione (TMHD) in a suitable solvent such as N-methyl-pyrrolidinone (NMP), at elevated temperature, such as between 80° C. and 110° C., for example according to the procedure described in Ley V. S. and Thomas A. W., (2003) Angew. Chem. Int. Ed. 42, 5400-5449.

Scheme 11

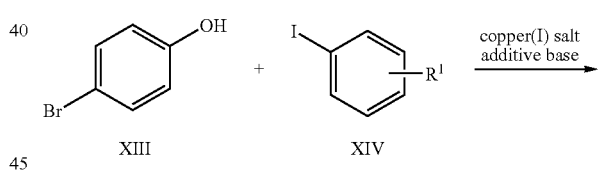

Compounds of Formula Ib, which are compounds of Formula I wherein $R^1$ represents fluoro, chloro, $CF_3$ or $OCF_3$; $R^4$ represents halo; $R^2$ represents methyl; and $R^3$ represents —$CH_2OH$, may be prepared from compounds of Formula XV, wherein $R^1$ represents fluoro, chloro, $CF_3$ or $OCF_3$, according to Scheme 12 by reaction of XV with an appropriate halogenating agent such as a halosuccinimide (NBS, NCS), trichloroisocyanuric acid (TCCA) or bromine in a suitable solvent such as a mixture of dichloromethane and methanol.

Scheme 12

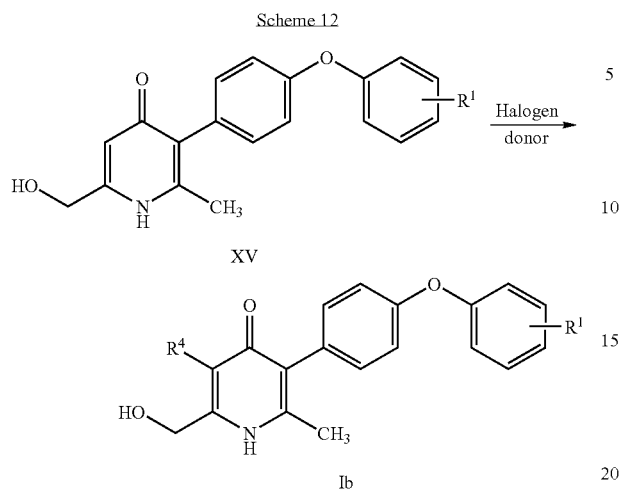

Compounds of Formula XV may be prepared from compounds of Formula XVI, wherein $R^1$ represents fluoro, chloro, $CF_3$ or $OCF_3$; according to Scheme 13 by treatment of compound XV with aqueous ammonia in a suitable solvent such as ethanol or methanol, suitably with heating under pressure, optionally in the presence of microwave radiation. In one aspect, the reaction is carried out in a steel reactor at elevated temperature for a period of between 1 h and 8 h. In another aspect the reaction is carried out at elevated temperature in a microwave oven, e.g. for a period of 30-90 minutes.

Scheme 13

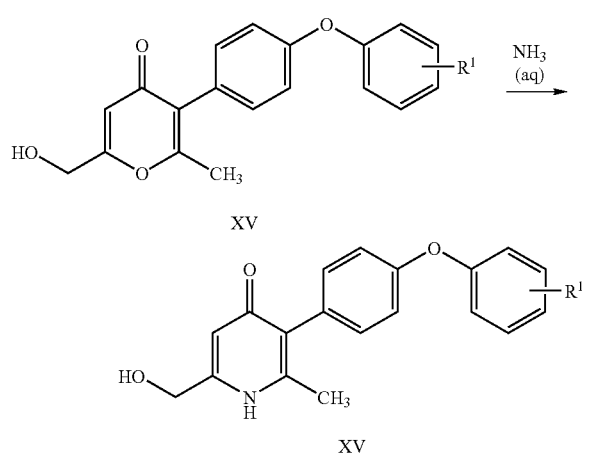

Compounds of Formula XV may be prepared using a Suzuki cross-coupling reaction between the compounds of Formula XVII, and boronic acid compounds of Formula V, wherein $R^1$ represents fluoro, chloro, $CF_3$ or $OCF_3$, according to Scheme 14. The compounds of Formula IV may be heated, for example at a temperature between 50° C. and 100° C., with V in an appropriate solvent such as toluene, ethanol, DMF or a mixture thereof, in the presence of a base such as sodium carbonate or potassium carbonate, and a suitable palladium catalyst. In one aspect, the palladium catalyst is Bis(triphenylphosphine)palladium(II)chloride.

Scheme 14

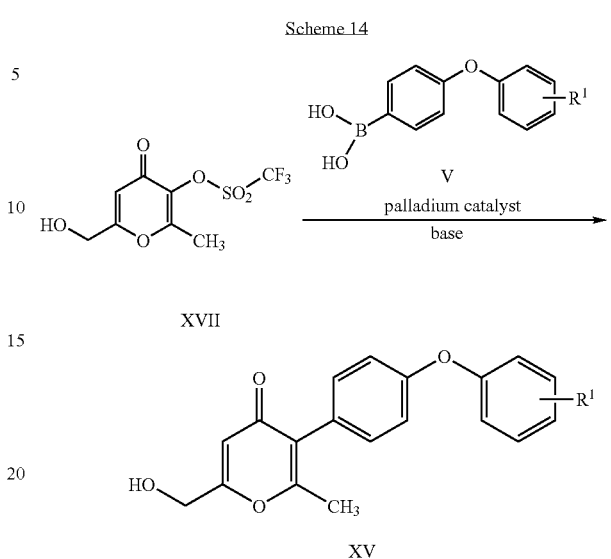

Compounds of Formula XVII may be prepared from compounds of Formula XVIII, according to Scheme 15 by treatment of XVII with a mild trifluoromethanesulfonylating agent in a suitable solvent such as dimethylformamide in the presence of a suitable base such as sodium or potassium carbonate. In one aspect, the trifluoromethanesulfonylating agent is N-phenyl-trifluoromethanesulfonimide.

Scheme 15

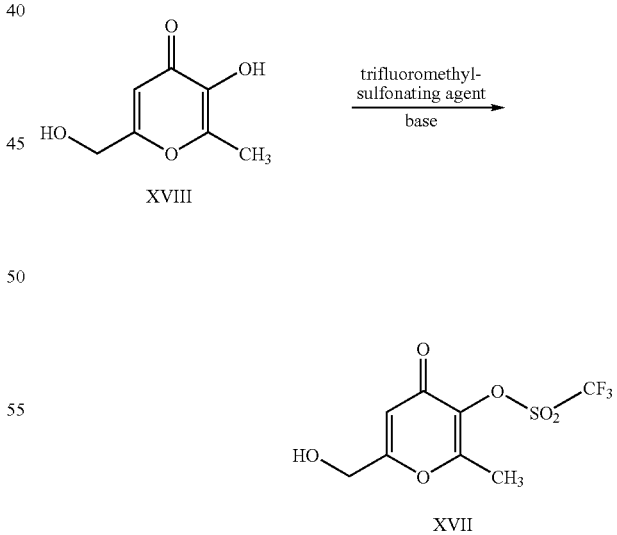

The compound of Formula XVIII may be prepared from the compound of Formula XIX according to Scheme 16 by reaction of XVIII with zinc in the presence of conc. HCl in a suitable solvent, such as water, at elevated temperature, for example between 50° C. and 90° C.

Scheme 16

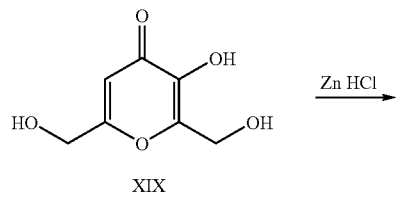

XIX

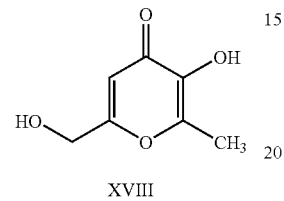

XVIII

The compound of Formula XIX may be prepared from the compound of Formula X, according to Scheme 17. Compound XIX may be treated with formaldehyde in the presence of a suitable base, such as aqueous sodium hydroxide.

Scheme 17

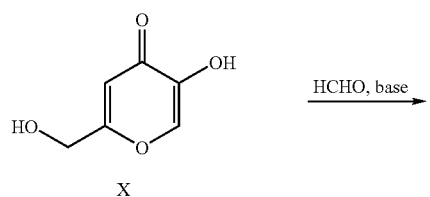

X

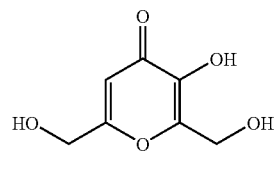

XIX

Compounds of Formula Ic, which are compounds of Formula I wherein $R^1$ represents halo, $CF_3$ or $OCF_3$; $R^4$ represents halo, $R^2$ represents —HC=N—$OR^5$; and $R^3$ represents methyl; and $R^5$ represents H or $C_{1-3}$alkyl; may be prepared from compounds of Formula XX, wherein $R^1$ represents halo, $CF_3$ or $OCF_3$; and $R^4$ represents halo; according to Scheme 18 by reaction of XX with $NH_2OR^5$.HCl,. wherein $R^5$ represents H or $C_{1-3}$alkyl; in the presence of a suitable base, such as pyridine, in a suitable solvent such as EtOH at elevated temperature, for example between 50° C. and reflux.

Scheme 18

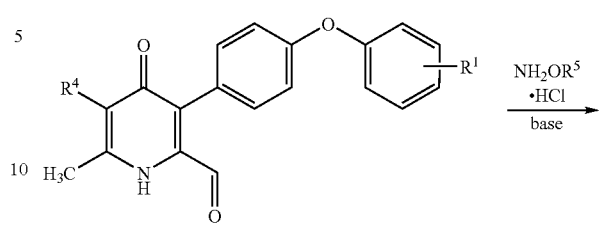

XX

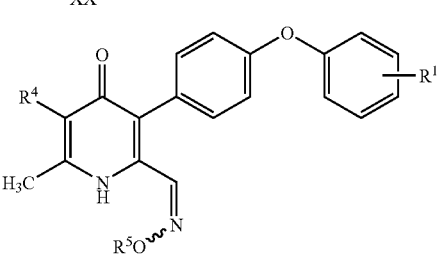

Ic
stereochemistry of
double bond not known

Compounds of Formula XX may be prepared from compounds of Formula Ia by an oxidation reaction according to Scheme 19, by treatment of Ia with a suitable oxidising agent such as sulfur trioxide-pyridine complex in the presence of a base such as triethylamine, in a suitable solvent, for example a mixture of DMSO and DCM.

Scheme 19

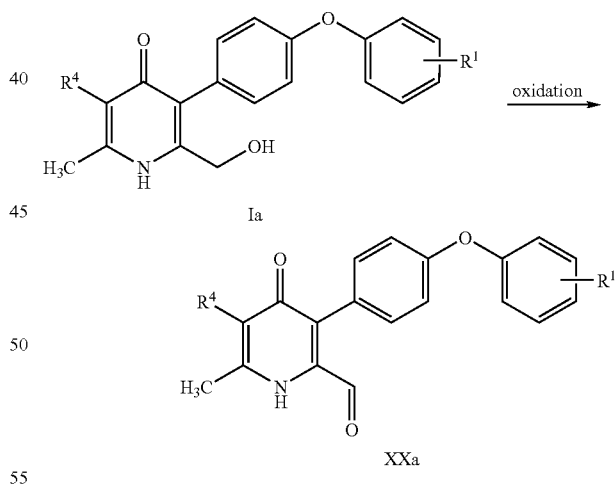

Compounds of Formula Id, which are compounds of Formula I wherein $R^1$ represents halo, $CF_3$ or $OCF_3$; $R^4$ represents halo; $R^2$ represents methyl; $R^3$ represents —HC=N—$OR^5$; and $R^5$ represents H or $C_{1-3}$alkyl; may be prepared from compounds of Formula XXI, wherein $R^1$ represents halo, $CF_3$ or $OCF_3$; and $R^4$ represents halo; according to Scheme 20 by reaction of XXI with $NH_2OR^5$.HCl,. wherein $R^5$ represents H or $C_{1-3}$alkyl; in the presence of a suitable base, such as pyridine, in a suitable solvent such as EtOH at elevated temperature, for example between 50° C. and reflux.

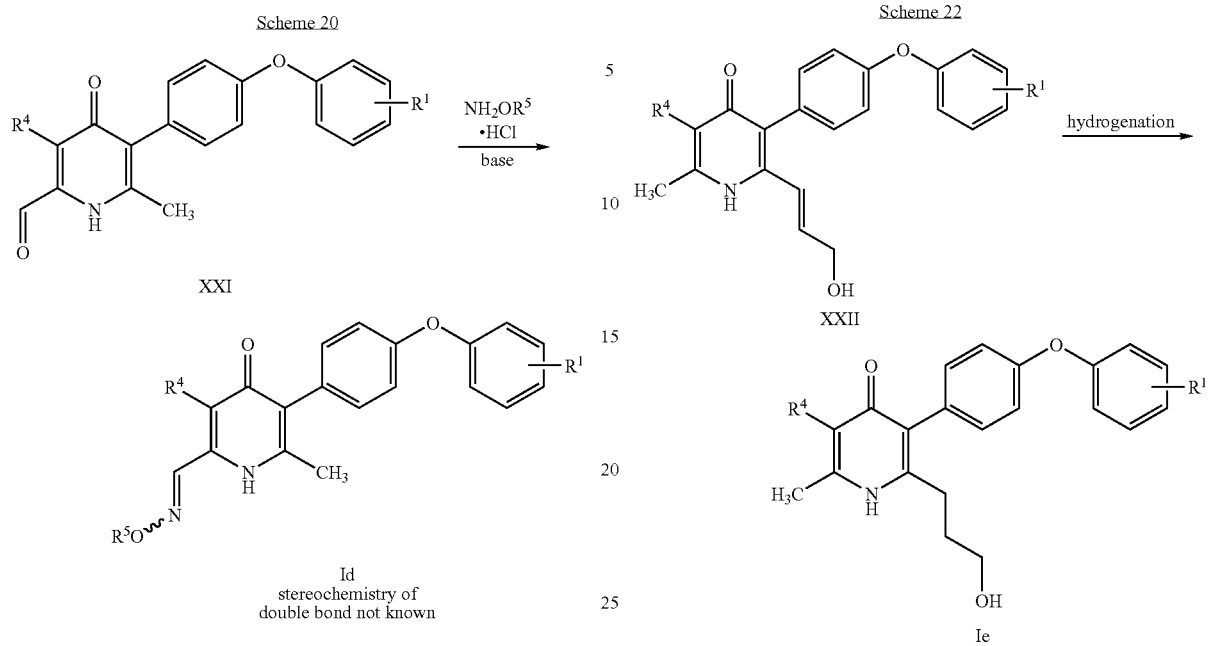

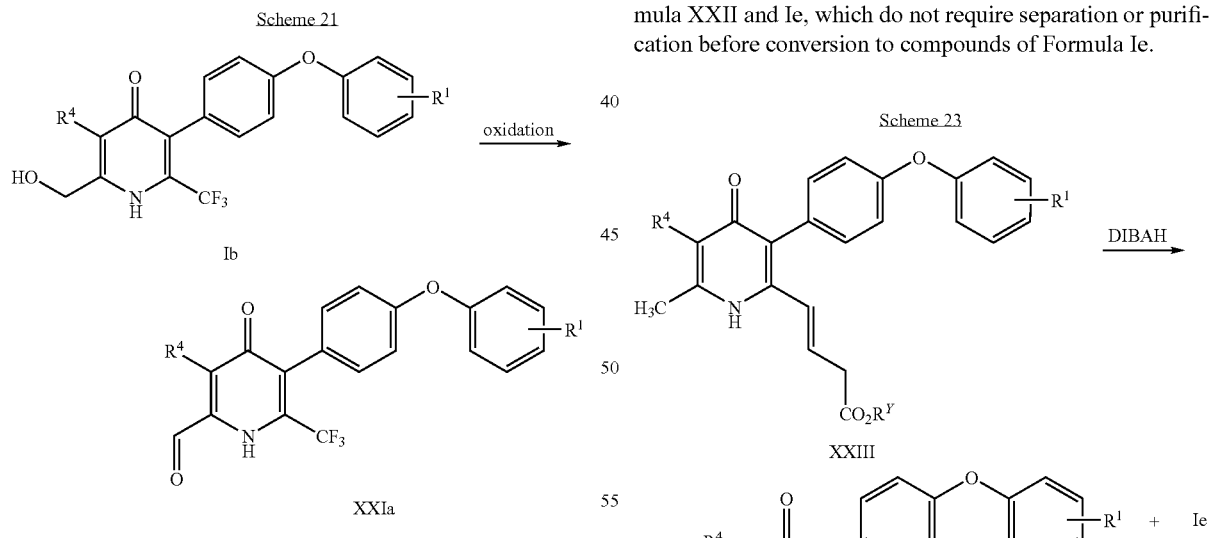

Compounds of Formula XXI may be prepared from compounds of Formula Ib by an oxidation reaction according to Scheme 21, by treatment of Ia with a suitable oxidising agent such as sulfur trioxide-pyridine complex in the presence of a base such as triethylamine, in a suitable solvent, for example a mixture of DMSO and DCM.

Compounds of Formula Ie, which are compounds of Formula I wherein $R^1$ represents fluoro, chloro, $CF_3$ or $OCF_3$; $R^4$ represents halo; $R^2$ represents —$(CH_2)_n$OH, wherein n represents 3; and $R^3$ represents methyl; and $R^5$ represents H or $C_{1-3}$alkyl; may be prepared from compounds of Formula XXII, wherein $R^1$ represents fluoro, chloro, $CF_3$ or $OCF_3$; and $R^4$ represents halo; according to Scheme 22 by hydrogenation of XXII in the presence of a suitable catalyst, for example palladium on charcoal, in a suitable solvent, such as EtOAc.

Compounds of Formula XXII may be prepared from compounds of Formula XXIII, wherein $R^1$ represents fluoro, $CF_3$ or $OCF_3$; $R^4$ represents halo; and $R^Y$ represents alkyl, for example methyl, ethyl or tert-butyl, according to Scheme 23, by reaction of XXIII with DIBAH in a suitable solvent such as THF with cooling, for example between 20° C. and −20° C. This reaction may produce a mixture of compounds of Formula XXII and Ie, which do not require separation or purification before conversion to compounds of Formula Ie.

Compounds of Formula XXIII may be prepared from compounds of Formula XX as defined above, according to Scheme 24 by a Wittig reaction of XX by reaction with (carbalkoxymethylene)-triphenylphosphorane Ph$_3$P=CHCO$_2$R$^Y$, wherein R$^Y$ represents alkyl, for example methyl, ethyl or tert-butyl, in a suitable solvent such as DCM.

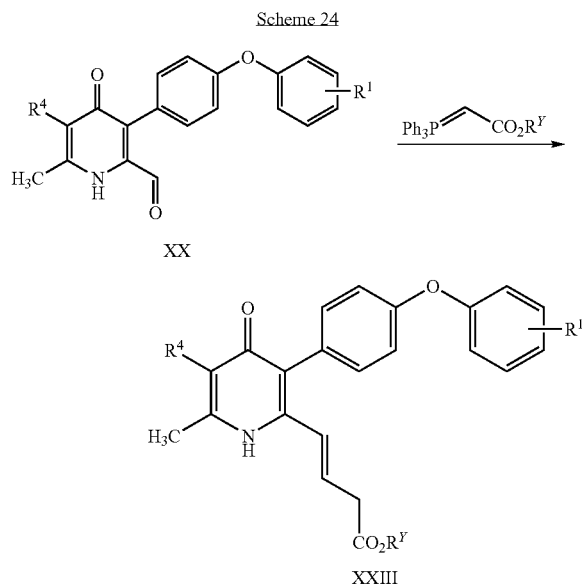

Compounds Formula I wherein R$^1$ represents fluoro, chloro, CF$_3$ or OCF$_3$; R$^4$ represents halo; R$^2$ represents —(CH$_2$)$_n$OH, wherein n represents 2 or 4; and R$^3$ represents methyl; and R$^5$ represents H or C$_{1-3}$alkyl, may be prepared using an analogous procedure to that described in Schemes 22-24 for Formula Ie, that is, by means of a Wittig reaction of compounds XX, followed by reduction of the thus-formed alkene, for example by hydrogenation.

Compounds of Formula II may alternatively be prepared from compounds of Formula XXIV, wherein R$^1$ represents halo, CF$_3$ or OCF$_3$, according to Scheme 25 by reductive opening of XXIV and subsequent cyclisation of the intermediate enamine promoted by, for example i) hydrogen in the presence of a suitable catalyst such as palladium on activated charcoal, or ii) by using hexacarbonylmolybdenum in a suitable solvent such as EtOH.

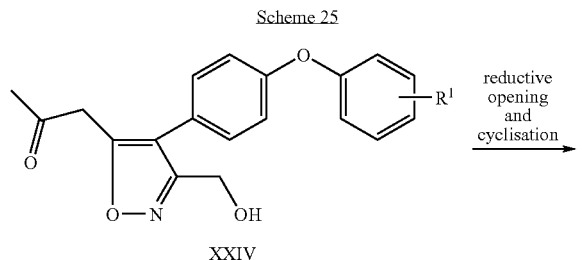

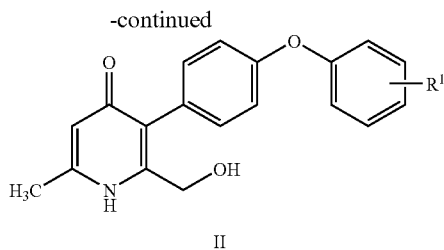

Compounds of Formula XXIV may be prepared from compounds of Formula XXV, wherein R$^1$ represents halo, CF$_3$ or OCF$_3$, by an acylation reaction according to Scheme 26. Compounds XXV may be treated with a suitable base such as either n-BuLi or LDA, or a mixture of n-BuLi and LDA optionally in the presence of N,N-diisopropylamine and a suitable lithium salt such as lithium chloride, followed by treatment with an acylating agent, such as N-methoxy-N-methyl-acetamide or ethyl acetate, at reduced temperature, such as −60° C. to −78° C., in a suitable solvent such as THF.

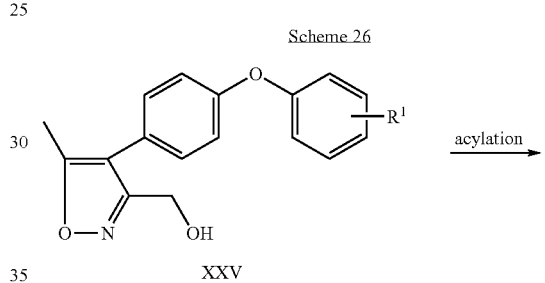

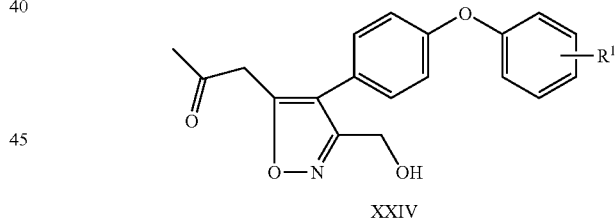

Compounds of Formula II may be obtained from compounds of Formula XXV, without isolation and purification of intermediate compounds of Formula XXIV.

Compounds of Formula XXV may be prepared by means of a coupling reaction between a compound of Formula XXVI and Formula V, wherein R$^1$ represents halo, CF$_3$ or OCF$_3$, according to Scheme 27. Compounds XXVI and V may be reacted together in the presence of a suitable catalyst such as palladium on activated charcoal or bis(triphenylphosphine)palladium(II)chloride in the presence of a suitable base such as sodium hydrogencarbonate or sodium carbonate, in a suitable solvent such as EtOH or a mixture of EtOH and toluene, at elevated temperature, such as 70° C. to 90° C.

Scheme 27

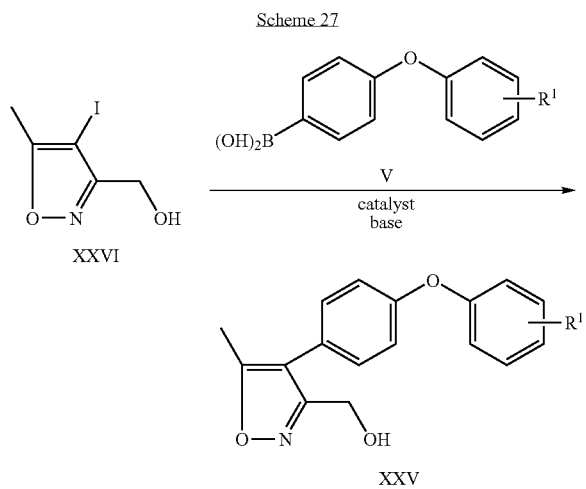

The compound of Formula XXVI may be prepared by an iodination reaction of a compound of Formula XXVII according to Scheme 28. Compound XXVII may be treated with iodine in the presence of a suitable catalyst such as silver trifluoroacetate, in a suitable solvent such as DCM, under elevated temperature, for example 30° C. to 60° C. or alternatively with iodine monochloride in a suitable solvent such as water in the presence of a strong organic acid such as trifluoroacetic acid at elevated temperature, for example 60-70° C.

Scheme 28

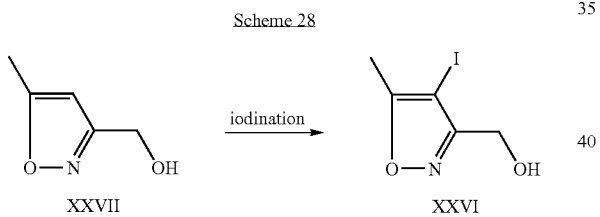

Compound XXVII may be prepared by reduction of compound XXVIII, which is commercially available, according to Scheme 29. Compound XXVIII may be treated with a suitable reducing agent, for example sodium borohydride, in a suitable solvent such as EtOH.

Scheme 29

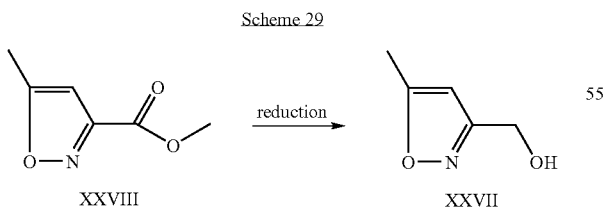

It will be readily apparent to those skilled in the art that further compounds of Formula I may be prepared using methods analogous to those outlined above, or by reference to the experimental procedures detailed in the Examples provided herein, or by using methods analagous to those previously reported in PCT Patent Application No. WO 91/13873 A1.

Those skilled in the art will appreciate that in the preparation of the compound of Formula I or a pharmaceutically acceptable derivative thereof, it may be necessary and/or desirable to protect one or more sensitive groups in the molecule or the appropriate intermediate to prevent undesirable side reactions. Suitable protecting groups for use according to the present invention are well known to those skilled in the art and may be used in a conventional manner. See, for example, "Protective groups in organic synthesis" by T. W. Greene and P. G. M. Wuts (John Wiley & sons 1991) or "Protecting Groups" by P. J. Kocienski (Georg Thieme Verlag 1994). Examples of suitable amino protecting groups include acyl type protecting groups (e.g. formyl, trifluoroacetyl, acetyl), aromatic urethane type protecting groups (e.g. benzyloxycarbonyl (Cbz) and substituted Cbz), aliphatic urethane protecting groups (e.g. 9-fluorenylmethoxycarbonyl (Fmoc), t-butyloxycarbonyl (Boc), isopropyloxycarbonyl, cyclohexyloxycarbonyl) and alkyl or aralkyl type protecting groups (e.g. benzyl, trityl, chlorotrityl). Examples of suitable oxygen protecting groups may include for example alky silyl groups, such as trimethylsilyl or tert-butyldimethylsilyl; alkyl ethers such as tetrahydropyranyl or tert-butyl; or esters such as acetate.

EXAMPLES

The following examples illustrate the invention. These examples are not intended to limit the scope of the invention, but rather to provide guidance to the skilled artisan to prepare and use the compounds, compositions, and methods of the invention. While particular embodiments of the invention are described, the skilled artisan will appreciate that various changes and modifications can be made without departing from the spirit and scope of the invention.

Experimental Section

Intermediate 1

(Bioorganic & Medicinal Chemistry 9, 2001, 563-573)

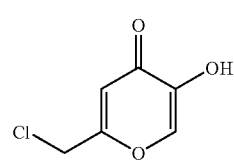

2-(chloromethyl)-5-hydroxy-4H-pyran-4-one

To Kojic acid (FLUKA, 1 g) was added thionyl chloride (ALDRICH, 1.027 mL). The yellow mixture was stirred at room temperature for 2 h. The precipitate was filtered, then washed with hexane and vacuum dried to afford 1.08 g of the title compound as a pale yellow solid.

$^1$H-NMR(δ, ppm, DMSO-d$_6$): 9.28(bd, 1H); 8.12(s,1H); 6.56(s, 1H); 4.65(s, 2H)

Intermediate 2

(Bioorganic & Medicinal Chemistry 9, 2001, 563-573)

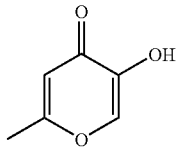

5-hydroxy-2-methyl-4H-pyran-4-one

To a suspension of Intermediate 1 (1.07 g) in water (30 mL) at 50° C. was added zinc dust (PANREAC, 871 mg). The mixture was heated at 70° C. for 1 h. Then HCl conc. (5 mL) was added dropwise and the mixture heated at 70-80° C. for 5 h. The excess zinc was removed by hot filtration and the pale yellow filtrate poured onto a mixture ice/water. The water layer was extracted with dichloromethane (3×30 mL) and the combined organic extracts dried over $Na_2SO_4$. Elimination of the solvent in vacuo gave 0.53 g of the title compound as a pale yellow solid.

$^1$H-NMR($\delta$, ppm, $CDCl_3$): 7.76(s, 1H); 6.24(s,1H); 2.28(s, 3H)

Intermediate 3

(Bioorganic & Medicinal Chemistry 9, 2001, 563-573; U.S. Pat. No. 6,426,418 B1)

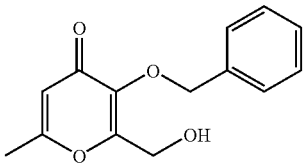

2-(hydroxymethyl)-6-methyl-3-[(phenylmethyl)oxy]-4H-pyran-4-one

A 1 L 3-necked round bottom flask was equipped with a mechanical stirrer and a dropping funnel. 1N NaOH (498 mL) was added to the flask followed by Intermediate 2 (57.15 g) portionwise. The reddish mixture was cooled in an ice bath (approx 30 min) and 37% aqueous formaldehyde solution (ALDRICH, 37.36 mL) was added dropwise (over 30 min) and the solution allowed to stir at room temperature for 18 h. The mixture was cooled at 0° C. and tetra-N-butylammonium bromide (ALDRICH, 365 mg) was added, followed by benzyl bromide (ALDRICH, 59.2 mL). The solution was heated at 60° C. for 2 h, then cooled to room temperature and stirred overnight and extracted with dichloromethane (3×500 mL). The combined organic extracts were washed with saturated aqueous NaCl (1×500 ml) and dried over $Na_2SO_4$, filtered and concentred in vacuo to give 117 g of a pale yellow solid. This solid was triturated with 80:20 EtOAc/hexane (250 mL), then filtered. This procedure was repeated with 70:30 EtOAc/hexane (250 mL) to afford 84.15 g of the title compound as a white solid after drying under vacuum.

$^1$H-NMR($\delta$, ppm, DMSO-$d_6$): 7.38(m, 5H); 6.25(s,1H); 5.43(t, 1H); 5.00(s, 2H); 4.25(d, 2H); 2.25(s, 3H)

Intermediate 4

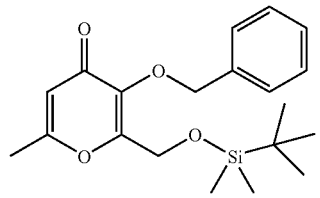

2-({[(1,1-dimethylethyl)(dimethyl)silyl]oxy}methyl)-6-methyl-3-[(phenylmethyl)oxy]-4H-pyran-4-one In a 2 L reactor was introduced Intermediate 3 (66.65 g) and dry N,N-dimethylformamide (500 mL). The mixture was stirred under nitrogen atmosphere to obtain a solution, then imidazole (55.28 g) and tert-butyldimethylsilyl chloride (48.94 g) were added, followed by addition of dry N,N-dimethylformamide (50 mL). After stirring for 3 h, ethyl acetate (900 mL) and 1 N $NH_4Cl$ (700 mL) were added. The two layers were partitioned and the organic layer washed with 1 N $NH_4Cl$ (2×900 mL) and brine (900 mL), dried over $Na_2SO_4$, filtered and concentrated to dryness under vacuum to give 103.68 g of the title compound as a pale yellow oil.

$^1$H-NMR($\delta$, ppm, $CDCl_3$): 7.35(m, 5H); 6.20(s,1H); 5.16 (s, 2H); 4.39(s, 2H); 2.62(s, 3H); 0.87(s, 9H); 0.04 (s, 6H)

Intermediate 5

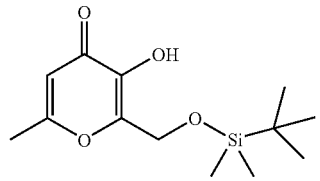

2-({[(1,1-dimethylethyl)(dimethyl)silyl]oxy}methyl)-3-hydroxy-6-methyl-4H-pyran-4-one To a solution of Intermediate 4 (23.71 g) in ethyl acetate (600 mL) under $N_2$ atmosphere was added palladium 10% w/w on activated charcoal (FLUKA, 700.9 mg). The mixture was hydrogenated at $1.8 \times 10^5$ Pa (1.8 bars) for 3 hours. The catalyst was removed by filtration and the solvent evaporated to dryness under vacuum to afford 16.72 g of the title compound.

¹H-NMR(δ, ppm, CDCl₃): 6.43(bd, 1H); 6.23(s,1H); 4.70 (s, 2H); 2.32(s, 3H); 0.91 (s, 9H); 0.12 (s, 6H)

Intermediate 6

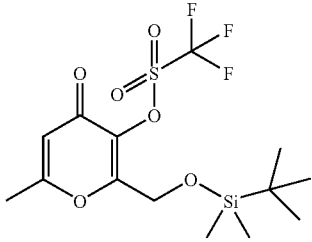

2-({[(1,1-dimethylethyl)(dimethyl)silyl]
oxy}methyl)-6-methyl-4-oxo-4H-pyran-3-yl trifluo-
romethanesulfonate In a 500 mL round bottom flask was introduced Intermediate 5 (16.72 g) in dry N,N-dimethylformamide (170 mL) and the solution stirred under N₂ atmosphere for 10 min. Then N-phenyltrifluoromethanesulfonimide (FLUKA, 23.85 g) and powdered potassium carbonate (ALDRICH, 10.68 g) were added in portionwise. After stirring for 1.5 h, potassium carbonate was removed by filtration and washed with tert-butyl-methyl-ether (300 mL). The filtrate was diluted with 100 mL of tert-butyl-methyl-ether and washed with 1N NH₄Cl (2×400 mL). The aqueous layer was extracted with tert-butyl-methyl-ether (200 mL). The combined organic extracts were washed with Na₂CO₃ (3×400 mL) and brine (400 mL), dried over MgSO₄, filtered and concentrated in vacuo to give 24.7 g of the title compound as a pale orange solid.
¹H-NMR(δ, ppm, CDCl₃): 6.29(s, 1H); 4.6624(s, 2H); 2.34(s, 3H); 0.92 (s, 9H); 0.13 (s, 6H)

Intermediate 7a

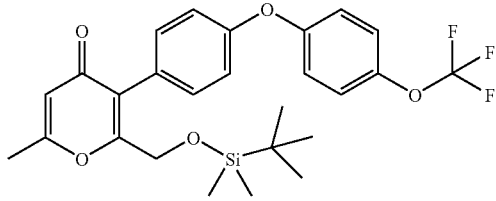

2-({[(1,1-dimethylethyl)(dimethyl)silyl]
oxy}methyl)-6-methyl-3-[4-({4-[(trifluoromethyl)
oxy]phenyl}oxy)phenyl]-4H-pyran-4-one In a 1 L round bottom flask were placed Intermediate 6 (11.8 g) and dry toluene (90 mL) and the resulting solution was deoxygenated by bubbling argon through it for 15 min. Bis(triphenylphosphine)palladium(II)chloride (ALDRICH, 1.03 g) was added and the mixture was deoxygenated again by bubbling argon through it for 30 min. Then a solution of Intermediate 19 (10.5 g) in dry ethanol (200 mL) was added. Finally, sodium carbonate (12.45 g) was added. After heating for 2 h and 45 min. at 80° C. under argon atmosphere, the mixture was stirred at room temperature overnight, then filtered and concentrated to dryness under vacuum. The crude product was dissolved in tert-butylmethylether (700 mL) and washed with 1N NaOH (2×500 mL), H₂O (500 mL) and brine (450 mL), dried over MgSO₄, filtered and concentrated to afford a dark solution which was filtred through a pad of celite. The resulting solution was concentrated to dryness to afford a dark oily residue which was purified by column chromatography on silica gel eluting with mixtures of ethyl acetate/hexane (0-50%). 10.3 g of the title compound were obtained as a brown solid.
¹H-NMR(δ, ppm, CDCl₃): 7.28(d, 2H); 7.20(d, 2H); 7.07-7.02(m, 4H); 6.25(s, 1H); 4.39(s, 2H); 2.33(s, 3H); 0.89(s, 9H); 0.05(s, 6H)

Intermediate 7b

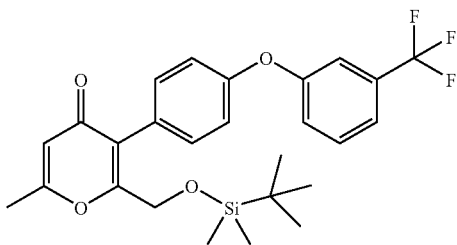

2-({[(1,1-dimethylethyl)(dimethyl)silyl]
oxy}methyl)-6-methyl-3-(4-{[3-(trifluoromethyl)
phenyl]oxy}phenyl)-4H-pyran-4-one In a 25 mL 2-neck round bottom flask were placed Intermediate 6 (500 mg) and dry toluene (4 mL) and the resulting solution was deoxygenated by bubbling argon through it for 15 min. Bis(triphenylphosphine)palladium(II)chloride (ALDRICH, 43.5 mg) and a solution of Intermediate 20 (420 mg) in dry ethanol (9 mL) were added and the resulting mixture was deoxygenated again by bubbling argon for 15 min, then sodium carbonate (525 mg) was added. After 3 h 15 minutes heating at 80° C. under argon atmosphere the mixture was cooled to room temperature, filtered, washed with toluene/methanol and concentrated to dryness. The crude product was dissolved in tert-butyl-methyl ether and washed with 1 N NaOH (2×), H₂O and NaOH, dried over MgSO₄, filtered and concentrated to dryness. The caramel oily residue was purified by column chromatography on silica gel eluting with mixtures ethyl acetate/hexane (0-70%). 460 mg of the title compound were obtained as a caramel oil.

¹H-NMR(δ, ppm, CDCl₃): 7.46(m, 1H); 7.36(m, 1H); 7.32-7.29(m, 3H); 7.24-7.20(m, 1H); 7.05(d, 2H); 6.25(s, 1H); 4.39(s, 2H); 2.33(s, 3H); 0.89(s, 9H); 0.04(s, 6H)

Intermediate 8a

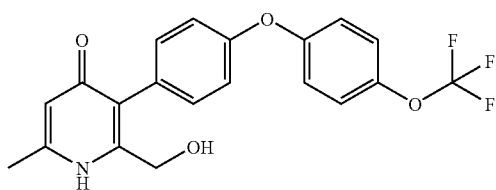

2-(Hydroxymethyl)-6-methyl-3-[4-({4-[(trifluoromethyl)oxy]phenyl}oxy)phenyl]-4(1H)-pyridinone Method A To a solution of Intermediate 7a (10.1 g) in ethanol (60 mL) was added 30% aqueous ammonia (200 mL). The suspension obtained was placed into a steel reactor and heated at 140° C. under 20 bars (300 psi) pressure for 8.5 h, then allowed to cool to room temperature overnight. The precipitate was filtered and washed with H₂O (700 mL) and ethyl acetate (20 mL), and dried under vacuum to afford 5.39 g of the title compound as a grey powder after drying under vacuum. ¹H-NMR(δ, ppm, DMSO-d₆): 10.84(bd, 1H); 7.39(d, 2H); 7.21(d, 2H); 7.12(d, 2H); 7.02(d, 2H); 5.98(s, 1H); 5.49(bd, 1H); 4.22(s, 2H); 2.24(s, 3H).

Method B

A solution of Intermediate 23 (0.365 g) in dry THF (10 ml) was cooled to −75° C. under Argon atmosphere. A solution of n-BuLi (1.4 ml, 1.78M in hexanes) was added and the mixture was stirred under Ar for 40 minutes, then 0.16 ml of N-methoxy-N-methyl-acetamide were added. The mixture was stirred at −75° C. for 3 h. HPLC analysis showed there was remaining starting material. Additional amounts of n-BuLi (1.4 ml, 1.78M in hexanes) and N-methoxy-N-methyl-acetamide (0.050 ml) were added consecutively and the mixture allowed to stir under Ar atmosphere at −75° C. for 1 h. 2N HCl (5 ml) was added and the mixture stirred at room temperature for 1 h, then water (50 ml) and t-BuOMe (50 ml) were added and the mixture partitioned. The organic layer was washed with water (50 ml), 10% NaHCO₃ (50 ml) and brine (50 ml). It was dried over Na₂SO₄, then concentrated to dryness to afford 0.425 g of an orange oil. It was dissolved in t-BuOMe (20 ml) and activated charcoal (0.3 g) was added. The mixture was stirred for 3 h at room temperature, filtered and evaporated to dryness. 0.38 g of crude material were obtained in this way, which were used for the next step without further purification. The crude product obtained as described above (0.38 g) was dissolved in EtOH (20 ml) and 10% palladium on activated charcoal (50 mg) was added onto the solution. The mixture thus obtained was hydrogenated for 6 h (2 bar pressure of hydrogen). Additional Pd(C) (50 mg) was added and the mixture hydrogenated under the same conditions for 18 h. Filtration of catalyst and evaporation of the solvent to dryness gave 0.375 g of crude product, which was dissolved in EtOAc (3 ml) and allowed to crystallize at room temperature overnight then in the fridge for 6 h. The product was filtered and washed with EtOAc and dried under vacuum. 0.17 g of the title compound were obtained as a white solid.

¹H-NMR(δ, ppm, DMSO-d₆): 10.84(bd, 1H); 7.39(d, 2H); 7.21(d, 2H); 7.12(d, 2H); 7.02(d, 2H); 5.98(s, 1H); 5.49(bd, 1H); 4.22(s, 2H); 2.24(s, 3H).

Method C

To a mixture of Intermediate 23 (0.548 g) and anhydrous lithium chloride (0.572 g) in dry tetrahydrofuran (15 ml) under argon atmosphere was added redistilled diisopropylamine (0.63 ml) and the mixture cooled to −75° C. A solution of n-BuLi (2 ml, 1.7M in hexanes) was added portionwise and the mixture was stirred under argon atmosphere at −75° C. for 1 hour, then N-methoxy-N-methylacetamide (0.225 ml) was added dropwise and the mixture stirred at −75° C. for 4 h. 2N HCl (10 ml) was added and the mixture stirred at room temperature for 0.5 h, then 1N HCl (75 ml) and t-BuOMe (75 ml) were added and the mixture partitioned. The organic layer was washed with 1N HCl (2×75 ml), 10% NaHCO₃ (75 ml), water (75 ml) and brine (75 ml). It was dried over Na₂SO₄, filtered and evaporated to dryness to afford 0.62 g of a pale brown oil as a crude product which was used for the next step without further purification.

The crude product (0.62 g) was dissolved in EtOH (25 ml) and 10% palladium on activated charcoal (60 mg) was added under nitrogen atmosphere onto the solution. The mixture thus obtained was hydrogenated for 8 h (2 bar H₂ pressure) in a Parr apparatus. Additional 10% palladium on activated charcoal (60 mg) was added and the mixture hydrogenated under the same conditions for 14 h.

The mixture was filtered through a Nylon 0.45 μm membrane and washed with 2:1 CH₂Cl₂/MeOH (3×5 ml). Elimination of the solvents to dryness gave 0.61 g of crude product which were dissolved in EtOAc (5 ml). To this solution was added 1 ml of hexane, then allowed to crystallize at room temperature then placed in the fridge overnight. The solid obtained was filtered off, washed with 3:2 hexane/ethyl acetate mixture (2×4 ml) and dried under vacuum to give 0.42 g of the title compound as a white solid.

¹H-NMR(δ, ppm, DMSO-d₆): 10.84(bd, 1H); 7.39(d, 2H); 7.21(d, 2H); 7.12(d, 2H); 7.02(d, 2H); 5.98(s, 1H); 5.49(bd, 1H); 4.22(s, 2H); 2.24(s, 3H).

Method D

A solution of Intermediate 23 (160 mg) in dry tetrahydrofuran (2 ml) was cooled to −78° C. under argon atmosphere. A solution of n-BuLi (0.44 ml, 2.5M in hexanes) was added dropwise and the mixture was stirred under argon atmosphere for 30 minutes at −78° C., then N-methoxy-N-methylacetamide (0.056 ml) was added and the mixture stirred. After approx 30 min the mixture turned into a thick gel and the reaction warmed up to −50° C. over 2 h to allow the mixture to become more fluid. The reaction mixture was warmed to −5° C. and 6N HCl (10 ml) was added. The mixture was stirred for 2 h, then neutralised (to approx. pH 7-8) with 10% NaHCO₃ and extracted with t-BuOMe three times. The combined organic layers were washed with brine, dried over anhydrous Na₂SO₄, filtered and concentrated under vacuum. The residue was purified by chromatography on silica gel eluting with EtOAc-Hexane 10:90 to 50:50 to afford 45 mg (28%) of the starting Intermediate 23 and 121 mg (67%) of 1-{3-(hydroxymethyl)-4-[4-({4-[(trifluoromethyl)oxy]phenyl}oxy)phenyl]-5-isoxazolyl}-2-propanone as yellow oil.

1H-NMR(δppm, DMSO-d₆): 7.34(d, 2H); 7.22(d, 2H); 7.06(d, 2H); 7.05(d, 2H); 4.72(d, 2H); 3.88(s, 2H); 2.45(bs, 2H); 2.26(s, 3H).

The product above described (0.114 g) was dissolved in EtOH (20 ml) and 10% palladium on activated charcoal (15 mg) was added onto the solution. The mixture thus obtained was hydrogenated for 6 h (2 bar H$_2$ pressure) in a Parr apparatus. Additional 10% palladium on activated charcoal (15 mg) was added and the mixture hydrogenated under the same conditions for 16 h.

The mixture was filtered through a nylon 0.45 μm filter. Elimination of the solvents to dryness gave 0.1 g of crude product which was triturated with EtOAc (1 ml). The solid obtained was filtered off and dried under vacuum to give 0.061 g of the title compound as a yellowish solid (Intermediate 8a).

$^1$H-NMR(δ, ppm, DMSO-d$_6$): 10.97(bd, 1H); 7.39(d, 2H); 7.21(d, 2H); 7.12(d, 2H); 7.02(d, 2H); 5.98(s, 1H); 5.49(bd, 1H); 4.22(s, 2H); 2.24(s, 3H).

Intermediate 8b

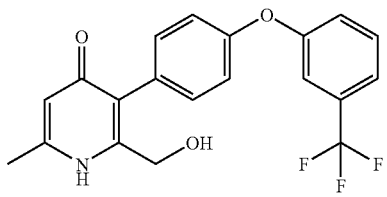

2-(Hydroxymethyl)-6-methyl-3-{4-[3-(trifluoromethyl)phenyl}oxy)phenyl]-4(1H)-pyridinone To a solution of Intermediate 7b (455 mg) in ethanol (13 mL) was added 30% aqueous ammonia (60 mL). The suspension obtained was placed into a steel reactor and heated at 140° C. After 8.5 h of heating, the reactor was allowed to cool to room temperature overnight. The organic solvent was removed under vacuum and the resulting aqueous solution freeze-dried to afford 316 mg of a brown solid. This solid was washed with ethyl acetate (12 mL), filtered and dried under vacuum to give 161 mg of the pure compound as a white solid.

$^1$H-NMR(δ, ppm, DMSO-d$_6$): 10.97(bd, 1H); 7.63(t, 1H); 7.48(d, 1H); 7.33-7.30(m, 2H); 7.24(d, 2H); 7.06(d, 2H); 5.96(s, 1H); 5.52(t, 1H); 4.22(s, 2H); 2.24(s, 3H)

Intermediate 9

(J. Am. Chem. Soc.; EN; 121; 30; 1999; 7020-7025.)

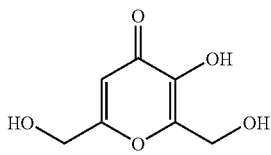

3-hydroxy-2,6-bis(hydroxymethyl)-4H-pyran-4-one

In a 100 mL round bottom flask were added Kojic acid (FLUKA, 5 g), 1N NaOH (39 mL) and H$_2$O (10 mL). The mixture was cooled (ice/water bath) and 37% aqueous formaldehyde (ALDRICH, 2.9 mL) was added dropwise. After 34 h at room temperature aditional 37% aqueous formaldehyde (ALDRICH, 0.5 mL) was added dropwise and the solution allowed to stir for 18 h. The mixture was acidified by adding concentrated HCl, and the solvent eliminated to dryness under vacuum to give a crude product which was treated with chilled water to afford a solid precipitated which was filtered and vacuum dried. 3.056 g of the title compound were obtained as a white solid. The filtrate was concentrated under vacuum and a second crop of solid separated. An additional 1.154 g of the title compound were obtained.

$^1$H-NMR(δ, ppm, CD$_3$OD): 6.46(s, 1H); 4.61 (s, 2H); 4.43 (s, 2H)

Intermediate 10

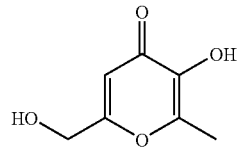

3-hydroxy-6-(hydroxymethyl)-2-methyl-4H-pyran-4-one

To a suspension of Intermediate 9 (6.56 g) in water (22.8 mL) at 50° C. was added zinc dust (PANREAC, 4.98 g) and HCl conc. (11.43 mL) dropwise and the mixture was heated at 70-80° C. for 5 h. The excess zinc was removed by hot filtration through celite and the filter cake washed with chilled water. To the aqueous solution was added solid NaCl until a solid separated. This solid was which was filtered off and dried under vacuum to obtain 3.16 g of the title compound.

$^1$H-NMR(δ, ppm, DMSO-d$_6$): 8.69(s, 1H); 6.26(s, 1H); 5.63(t, 1H); 4.26(d, 2H); 2.26(s, 3H)

Intermediate 11

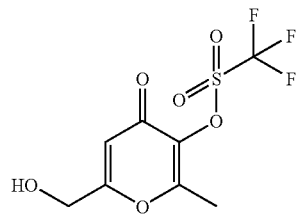

6-(hydroxymethyl)-2-methyl-4-oxo-4H-pyran-3-yl trifluoromethanesulfonate

To a solution of Intermediate 10 (180 mg) in dry N,N-dimethylformamide (9 mL) under N$_2$ atmosphere were added potassium carbonate (ALDRICH, 478 mg) and N-phenyltrifluoromethanesulfonimide (FLUKA, 412 mg). After stirring for 0.5 h at room temperature, 1N NH$_4$Cl was added and the mixture extracted with ethyl acetate. The organic layer was washed with 1 N NH$_4$Cl (4×), 0.5N NaOH and brine, dried over Mg$_2$SO$_4$, filtered and concentred in vacuo. The residue was purified by chromatography (96% CH$_2$Cl$_2$/MeOH) to afford 166 mg of the title compound as a white solid.

¹H-NMR(δ, ppm, CDCl₃): 6.57(s, 1H); 4.51(d, 2H); 2.83 (t, 1H); 2.42(s, 3H)

Intermediate 12a

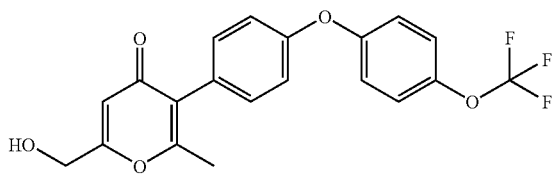

6-(hydroxymethyl)-2-methyl-3-[4-({4-[(trifluoromethyl)oxy]phenyl}oxy)phenyl]-4H-pyran-4-one In a 2-necked round bottom flask were placed Intermediate 11 (160 mg), dry toluene (1.7 mL) and dry ethanol (0.5 mL). The resulting solution was deoxygenated by bubbling N₂. Tetrakis(triphenylphosphine)palladium(0) (ALDRICH, 38 mg) followed by a solution of Intermediate 19 (215 mg) in dry ethanol (4 mL) and sodium carbonate (235 mg) were added. The mixture was deoxygenated under N₂ atmosphere and heated at 80° C. for 4 h. The mixture was concentrated to dryness, 1N NH₄Cl and ethyl acetate were added and stirred for 10 minutes. The aqueous layer was extracted with ethyl acetate and the combined organic extracts were washed with brine, dried over MgSO₄, filtered and concentred under vacuum. The crude product was purified by column chromatography (1%, 2% methanol/dichloromethane) to afford 202 mg of the title compound as orange oil.

¹H-NMR(δ, ppm, CDCl₃): 7.23-7.19(m, 4H); 7.08-7.02 (m, 4H); 6.49(s, 1H); 5.30(s, 1H); 4.50(d, 2H); 2.46(t, 1H); 2.24(s, 3H)

Intermediate 12b

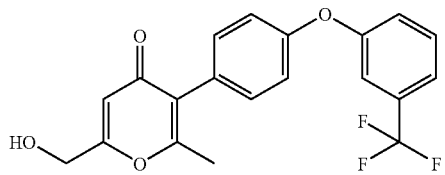

6-(hydroxymethyl)-2-methyl-3-(4-{[3(trifluoromethy)phenyl]oxy}phenyl)-4H-pyran-4-one Intermediate 12b was prepared by a method analogous to that described for Intermediate 12a using Intermediate 11 (2.3 g) in toluene (24 mL), Bis(triphenylphosphine)palladium(II) chloride (ALDRICH, 280 mg) as catalyst, Intermediate 20 (2.7 g) in EtOH (55.86 mL) and sodium carbonate (3.38 g). The mixture was heated at 85° C. for 40 minutes, cooled, filtered through a pad of celite, which was washed with ethyl acetate and the solvent evaporated. The crude product was dissolved in EtOAc, washed with NH₄Cl 1N (1×), H₂O (1×), NaHCO₃ sat. (1×) and NaCl (1×), dried (MgSO₄) and concentrated under vacuum. Purification by column chromatography (EtOAc-hexane 0-100%) gave a first fraction of 931 mg of the title compound along with an impure sample which was further re-purified by column chromatography to afford an additional 510 mg of the title compound as a yellow solid.

¹H-NMR(δ, ppm, CDCl₃): 7.49-7.33(m, 3H); 7.23(m, 3H); 7.05(d, 2H); 6.53(s, 1H); 4.51 (s, 2H); 2.25(s, 3H).

Intermediate 13a

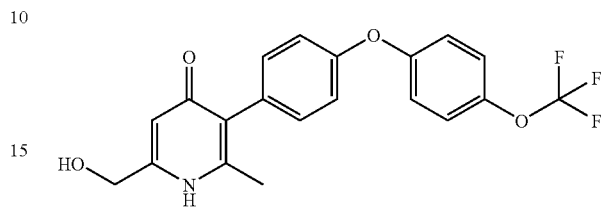

6-(hydroxymethyl)-2-methyl-3-[4-({4-[(trifluoromethyl)oxy]phenyl}oxy)phenyl]-4(1H)-pyridinone A suspension of 195 mg of Intermediate 12a in methanol (2 mL) was introduced into a microwave tube with magnetic stirring. 30% aqueous ammonia (3 mL) and was added and the resulting suspension heated at 140° C. for 30 minutes under microwave radiation. Upon cooling, the crude product was diluted with water and filtered under vacuum. The solid was washed with acetonitrile to give 92 mg of the title compound as an off-white solid. ¹H-NMR(δ, ppm, DMSO-d₆): 11.09(bd, 1H); 7.39(d, 2H); 7.19(d, 2H); 7.12(d, 2H); 7.02(d, 2H); 6.07(s, 1H); 5.51(bd, 1H); 4.33 (bd, 2H); 2.10(s, 3H)

Intermediate 13b

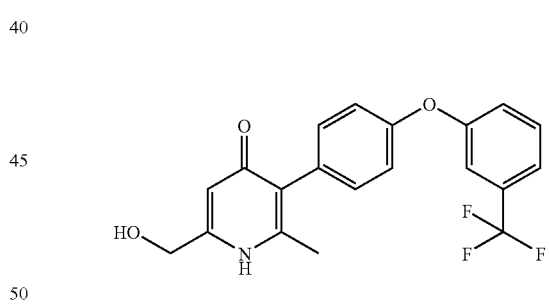

6-(hydroxymethyl)-2-methyl-3-(4-{[3-(trifluoromethyl)phenyl]oxy}phenyl)-4(1H)-pyridinone To a solution of Intermediate 12b (200 mg) in methanol (1.5 mL) was added commercial 30% aqueous ammonia (3.5 mL) with stirring. The reaction was run at 140° C. for 30 minutes under microwave radiation. Upon cooling, the crude product was diluted with water and filtered under vacuum. The solid was washed with acetonitrile to give 104 mg of the title compound as an off-white solid.

$^1$H-NMR(δ, ppm, DMSO-d$_6$): 11.08(bs, 1H); 7.62(m, 1H); 7.48(d, 1H); 7.32(m, 2H); 7.21(d, 2H); 7.06(d, 2H); 6.07(m, 1H); 5.5(m, 1H); 4.32(s, 2H); 2.09(s, 3H).

Intermediate 14

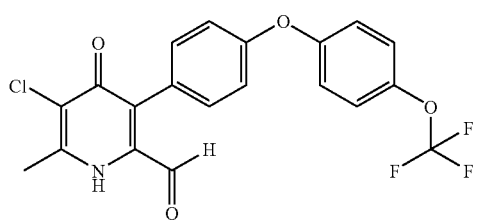

5-Chloro-6-methyl-4-oxo-3-[4-({4-[(trifluoromethyl)oxy]phenyl}oxy)phenyl]-1,4-dihydro-2-pyridinecarbaldehyde To a solution of Example 1 (0.506 g) in dichloromethane (5 mL) was added DMSO (3.49 mL) and triethylamine (1.26 mL) dropwise. This mixture was cooled to 0° C. to which was added sulphur trioxide-pyridine complex in small portions (0.947 g). The reaction temperature was allowed to warm to room temperature and the mixture stirred for 21 hours. The mixture was diluted with dichloromethane and washed with water (3×40 mL).

The organic phase was dried over anhydrous Na$_2$SO$_4$ and concentrated under vacuum to give brown oil which was purified by column chromatography on silica gel by using dichloromethane as first eluent, then mixtures methanol/dichloromethane v/v 1:600, 1:500, 1:400 and 1:200). A total amount of 424 mg of the title compound were obtained after evaporation of the solvent in the appropriate fractions.

$^1$H NMR (δ, ppm, CDCl$_3$): 9.66 (s, 1H), 9.03 (bs, 1H), 7.41 (d, 2H), 7.23 (d, 2H), 7.12-7.06 (m, 4H), 2.60 (s, 3H); [ES MS] m/z 424 (MH$^+$).

Intermediate 15

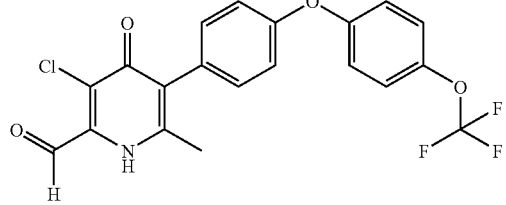

3-Chloro-6-methyl-4-oxo-5-[4-({4-[(trifluoromethyl)oxy]phenyl}oxy)phenyl]-1,4-dihydro-2-pyridinecarbaldehyde To a suspension of Example 3 (0.422 g) in dichloromethane (4.25 mL) was added under argon atmosphere anhydrous DMSO (3 mL). The resulting solution was cooled in an ice-water bath and triethylamine (1 mL) was added followed by sulphur trioxide-pyridine complex (0.788 g). The mixture was allowed to warm to room temperature overnight. After 20 h of stirring the mixture was washed with water (5×), dried over Na$_2$SO$_4$ and concentrated to dryness. 380 mg of the title compound were obtained as a yellow powder.

$^1$H-NMR(δ, ppm, CDCl$_3$): 10.33(s, 1H); 7.22(m, 4H); 7.06 (m, 4H); 2.30(s, 3H).

Intermediate 16

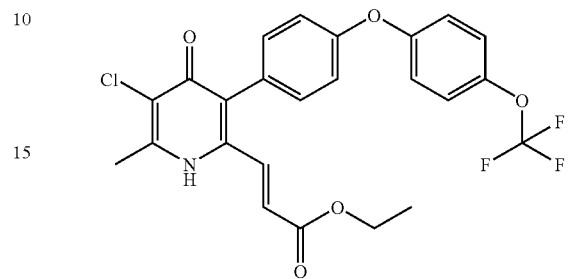

Ethyl (2E)-3-{5-chloro-6-methyl-4-oxo-3-[4-({4-[trifluoromethyl)oxy]phenyl}oxy)phenyl]-1,4-dihydro-2-pyridinyl}-2-propenoate To a solution of Intermediate 14 (0.154 g) in dichloromethane (7.20 mL) under argon atmosphere was added (carbethoxymethylene)-triphenylphosphorane (0.190 g). The reaction mixture was stirred at room temperature for 2 hours, then washed with water (3×5 mL). The organic layer was dried over anhydrous Na$_2$SO$_4$ and concentrated under vacuum to give a mixture of trans/cis α, β-unsaturated esters. The crude product was purified by column chromatography on silica gel (eluent CH$_3$OH/CH$_2$Cl$_2$ 0-5%). 0.058 g of the title product were obtained as a yellow solid.

$^1$H NMR (δ, ppm, CDCl$_3$): 13.41 (s, 1H), 7.26 (d, 2H), 7.20 (d, 2H), 7.08 (d, 2H), 7.03 (d, 2H), 6.72 (d, 1H), 6.00 (d, 1H), 4.23 (q, 2H), 2.56 (s, 3H), 1.37 (t, 3H)

Intermediate 17

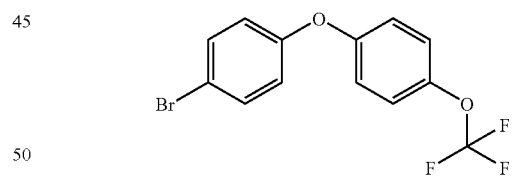

1-Bromo-4-({4-[(trifluoromethyl)oxy]phenyl}oxy)benzene

A solution of 4-bromophenol (0.173 g) in 4 mL of 1-methyl-2-pyrrolidone under argon atmosphere was treated with 4-(trifluoromethoxy)iodobenzene (0.313 mL), 2,2,6,6-tetramethylheptane-3,5-dione (0.046 mL) and caesium carbonate (0.652 g). The slurry was degassed by bubbling argon for 15 min and copper(I) chloride (0.099 g) was added. The reaction mixture was degassed by bubbling argon for 15 min, then heated to 100° C. under argon for 5 h. The reaction mixture was cooled to room temperature and added dropwise to 30 mL of tert-butyl-methyl-ether. The slurry was filtered and the solids washed with tert-butyl-methyl-ether (3×20 mL). The combined filtrates were washed subsequently with 1N NaOH (50 mL), water (50 mL), 2N HCl (50 mL), 1N HCl (50 mL), water (50 mL) and brine (50 mL). The resulting organic layer was dried over Na$_2$SO$_4$ and concentrated to give a crude product which was purified by column chromatography on silica gel eluting with hexane to afford 0.15 g of the title compound as a colourless liquid.

$^1$H-NMR(d, ppm, CDCl$_3$): 7.45(m, 2H); 7.20(m, 2H); 6.99 (m, 2H); 6.90(m, 2H)

Intermediate 18

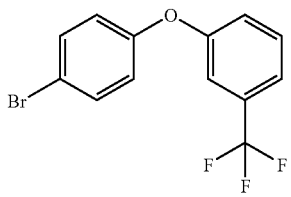

1-[(4-bromophenyl)oxy]-3-(trifluoromethyl)benzene

In a 2-neck round bottom flask were added 4-bromophenol (ALDRICH, 500 mg) and 1-methyl-2-pyrrolidone (ALDRICH, 12 mL) under argon atmosphere. Then 3-iodobenzyl-trifluoride (ALDRICH, 1.18 g), 2,2,6,6-tetramethyl-3,5-heptanedione (ALDRICH, 0.133 mL) and powdered caesium carbonate (ALDRICH, 1.88 g) were added and the mixture was stirred for 15 minutes under argon atmosphere. Finally, copper(I) chloride (ALDRICH, 143 mg) was added and the mixture was stirred for 20 minutes under argon atmosphere. The resulting mixture was heated at 105° C. for 3.5 h and cooled at room temperature. Tert-butyl-methyl ether (60 mL) was added, the mixture was stirred for 15 minutes, filtered to removed the solid (copper salts) and washed with tert-butyl-methyl-ether. The filtrated was washed with 2N HCl (70 mL), 1N HCl (70 mL), 2N NaOH (2×60 mL) and brine (70 mL), dried over MgSO$_4$, filtered and evaporated under vacuum to give 964 mg of the title compound.

$^1$H-NMR(δ, ppm, CDCl$_3$): 7.48(d, 2H); 7.44(d, 1H); 7.36 (d, 1H); 7.24(s, 1H); 7.15(m, 2H); 6.91(d, 2H)

Intermediate 19

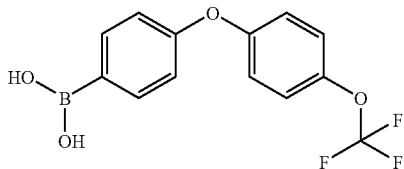

[4-({4-[(Trifluoromethyl)oxy]phenyl}oxy)phenyl]boronic acid

To a solution of Intermediate 17 (4.53 g) in dry tetrahydrofuran (100 mL) at −75° C. was added triisopropyl borate (4.1 mL). The mixture was cooled to −78° C. to which was added dropwise 1.47M n-butyllithium in hexanes (11.1 mL). The mixture was stirred for 3 hours at −75° C., then quenched by addition of 6N HCl (12 mL) and stirred overnight in a bath of acetone and solid carbon dioxide, during which time the reaction had warmed to room temperature. The mixture was partitioned between ethyl acetate (200 mL) and water (200 mL), the layers separated and the organic layer washed with water (2×200 mL) and brine (200 mL), then dried over Na$_2$SO$_4$, filtered and evaporated to dryness. The solid obtained was treated with 2N NaOH (60 mL), stirred for several minutes, diluted with water (250 mL) to dissolve the observed white solid precipitate, and the solution filtered through a 0.45 μm nylon filter. The filtrate was washed with pentane (2×200 mL), the aqueous layer acidified to pH 1.5 with 6N HCl and the precipitate filtered off, washed with water and dried under vacuum to give 3.23 g of the title compound as a pale yellow solid.

$^1$H-NMR(d, ppm, CDCl$_3$): 8.01(bs, 2H); 7.85-7.78(m, 2H); 7.43-7.33(m, 2H); 7.15-7.07 (m, 2H); 7.02-6.94(m, 2H).

Intermediate 20

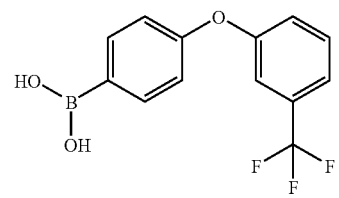

(4-{[3-(trifluoromethyl)phenyl]oxy}phenyl)boronic acid

In a 500 mL round bottom flask were added a solution of Intermediate 18 (17.576 g) in dry tetrahydrofuran (100 mL) under argon atmosphere, 100 mL more of tetrahydrofuran and triisopropyl borate (ALDRICH, 16.63 mL). The mixture was cooled at −78° C. and n-butyllithium 1.65 M (ALDRICH, 40.3 mL) was added dropwise. The solution was stirred at −78° C. for 4 h and 45 minutes, then 6N HCl (55 mL) was added dropwise and the mixture stirred at room temperature overnight. Tetrahydrofuran was removed at reduced pressure and tert-butyl-methyl-ether (500 mL) and water (400 mL) were added. The organic layer was washed with Na$_2$S$_2$O$_5$ (400 mL), H$_2$O (400 mL) and brine (400 mL), dried over MgSO$_4$, filtered and evaporated under vacuum. To the resulting crude product was added 2N NaOH (325 mL) in order to form the sodium salt and water (600 mL) to dissolve it. The aqueous solution was extracted with pentane (2×500 mL) to removed some impurities and it was acidified by addition of 2N HCl (325 mL, pH=1). The white precipitate was filtered, washed with water and dried under vacuum to give 11.0483 g of the title compound as a white solid.

$^1$H-NMR(δ, ppm, DMSO-d$_6$): 8.04(s, 2H); 7.83(d, 2H); 7.62 (m, 1H); 7.49(d, 1H); 7.30(m, 2H); 7.02(d, 2H)

Intermediate 21

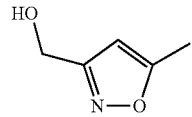

(5-methyl-3-isoxazolyl)methanol

To a suspension of methyl 5-methyl-3-isoxazolecarboxylate (9 g, available from ABCR) in dry ethanol (90 ml) in an ice bath under nitrogen, was added portionwise sodium borohydride (3.6 g) and the mixture was stirred at room temperature for 3 h. The mixture was cooled with an ice bath and hydrolized carefully by adding 1N HCl (120 ml) until pH<7. The mixture was concentrated under vacuum in order to eliminate ethanol and the resulting aqueous solution neutralized with aqueous NaOH (firstly 5N, then 1N), until pH 6-7. The aqueous solution was extracted with DCM (6×50 ml) and the combined organic layers washed with brine (50 ml), dried over sodium sulfate, filtered and concentrated to dryness to afford the title compound (6 g) as a yellowish oil. The aqueous layer was re-extracted with DCM (3×50 ml) and the new combined organic layers dried again over sodium sulphate, filtered and the solvent evaporated to dryness. An additional amount (1 g) of the title compound was obtained as a yellowish oil. Both samples (7 g total amount) were used together for the next step.

$^1$H-NMR($\delta$, ppm, CDCl3): 6.03(s, 1H); 4.70(s, 2H); 2.42 (s, 3H)

Intermediate 22

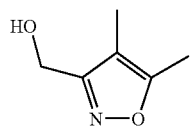

(4-iodo-5-methyl-3-isoxazolyl)methanol

Method A

To a suspension of silver trifluoroacetate (13.25 g) in dry DCM (175 ml) was added at room temperature a solution of Intermediate 21 (6.25 g) in dry DCM (25 ml). After 30 minutes of stirring Iodine (15.25 g) was added portionwise and the mixture stirred for 30 minutes at room temperature, then heated to 48° C. under nitrogen for 3 h. Additional amounts of silver trifluoroacetate (1.3 g) and Iodine (1.5 g) were added and heating continued for 2 h, then allowed to stir at room temperature overnight. The mixture was diluted with DCM (60 ml) and filtered off and washed with DCM (3×30 ml). The resulting filtrate and washings were washed successively with water (200 ml), 10% Na$_2$S$_2$O$_5$ (200 ml), 10% NaHCO$_3$ (200 ml), water (200 ml) and brine (200 ml), dried over Na$_2$SO$_4$, filtered and concentrated to dryness to afford 14.55 g of an oily material which became solid. It was triturated with heptane (8 ml) and the resulting solid filtered and dried under vacuum. A first crop (6.2 g) of the desired compound was obtained in this way as a white solid. The combined organic washings were evaporated to dryness to afford 7.5 g of an oily residue which was passed through a short pad of silica gel, eluting with hexane and hexane/EtOAc 4:1. Evaporation of solvent of the appropriate fractions gave an oily material which was dissolved in MeOH (15 ml) and treated with 1N HCl (10 ml) and 10% Na$_2$S$_2$O$_5$ (10 ml) for 30 minutes. The solvents were eliminated to dryness and the residue partitioned between EtOAc (150 ml) and 1N HCl (100 ml). The organic layer was washed successively with 10% Na$_2$S$_2$O$_5$ (100 ml), saturated NaHCO$_3$ (100 ml) and brine (100 ml), then dried over Na$_2$SO$_4$ and concentrated to dryness to afford 4.75 g of a yellowish solid, which was triturated with heptane (6 ml), filtered, washed with heptane (4 ml) and dried under vacuum to obtain a second crop (4.5 g) of the desired compound as a white solid.

Method B

To a suspension of ICl (6.3 g) in water (75 ml) was added the hydroxymethyl-methylisoxazole (3.4 g) followed by TFA (11.1 ml). The mixture was heated at 65° C. under nitrogen. After 2 h of heating, additional ICl (1 g) was added and the mixture heated for 2.5 h. The mixture was allowed to cool to room temperature, then diluted with water (150 ml) and treated with 10% Na$_2$S$_2$O$_5$ (25 ml). The mixture was made basic by addition of solid Na$_2$CO$_3$ (15 g) portionwise (pH=7.5-8.0), then extracted with dichloromethane (1×100 ml+2×75 ml). The combined organic layers were washed with water (50 ml) and brine (50 ml), dried over Na$_2$SO$_4$, filtered and concentrated to dryness to afford 6.58 g of the title compound as a whitish solid (91% yield).

$^1$H-NMR($\delta$, ppm, CDCl3): 4.68(d, 2H); 2.47(s, 3H); 2.12 (t, 1H)

Intermediate 23

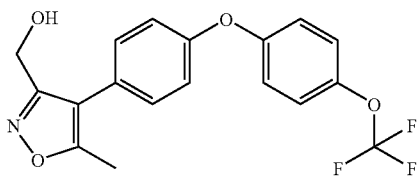

{5-methyl-4-[4-({4-[(trifluoromethyl)oxy]phenyl}oxy)phenyl]-3-isoxazolyl}methanol A mixture of Intermediate 22 (5.976 g), Intermediate 19 (7.97 g) and 10% palladium on activated charcoal (1.25 g) in ethanol (150 ml) was deoxygenated by bubbling nitrogen for 30 min, then 10% NaHCO$_3$ solution (75 ml) was added dropwise onto it. The mixture was heated to 85° C. for 5 h under nitrogen atmosphere, then allowed to cool to room temperature and stirred overnight. The mixture was filtered through a nylon membrane (0.45 um) and the filter cake washed with DCM/MeOH 2:1 (3×75 ml). 1N NaOH (15 ml) was added and the organic solvents removed under reduced pressure. A black solid appeared, which was eliminated by filtration. The filter cake was washed with some DCM/MeOH 2:1 mixture. Water (60 ml) was added and elimination of organic solvents continued to afford an aqueous suspension containing a solid precipitate. The solid was filtered, then washed with 1N NaOH (3×50 ml) and water (4×50 ml). Once it was dried under vacuum the solid was washed with heptane (3×50 ml) and finally dried. 8.828 g of the title compound were obtained as a white solid.

¹H-NMR(δ, ppm, CDCl₃): 7.37(m, 2H); 7.25(m, 2H); 7.06 (m, 4H); 4.72(d, 2H); 2.46(s, 3H); 2.11(t, 1H)

Example 1

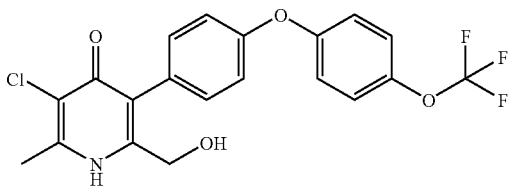

3-Chloro-6-(hydroxymethyl)-2-methyl-5-[4-({4-[(trifluoromethyl)oxy]phenyl}oxy)phenyl]-4(1H)-pyridinone In a 500 mL round bottom flask was dissolved Intermediate 8a (5.25 g) in dichloromethane/methanol v/v 2:1 (135 mL). The mixture was cooled at 0° C. under argon atmosphere with stirring and after 30 min trichloroisocyanuric acid (ALDRICH, 1.26 g) was added. The solution was stirred under nitrogen atmosphere for 50 minutes, filtered and washed with dichloromethane/methanol v/v 2:1 (60 mL). The filtrate was evaporated to dryness, 10% sodium carbonate was added (30 mL) and the mixture was stirred. The solid was filtered and washed with H₂O (100 mL), 10% Na₂CO₃ (2×30 mL), H₂O (2×50 mL) and acetonitrile (2×15 mL and 1×20 mL), dried under vacuum to give 4.66 g of the title compound as a off-white powder.

¹H-NMR δ ppm, DMSO-d₆: 11.50(bd, 1H); 7.40(d, 2H); 7.24(d, 2H); 7.14(d, 2H); 7.04(d, 2H); 5.58(bd, 1H); 4.23(s, 2H); 2.44(s, 3H). [ES MS] m/z 426 (MH+).

Example 2

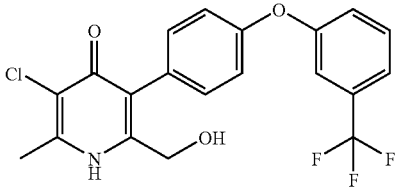

3-Chloro-6-(hydroxymethyl)-2-methyl-5-[4-({4-[(trifluoromethyl)oxy]phenyl}oxy)phenyl]-4(1H)-pyridinone In a 25 mL round bottom flask was dissolved Intermediate 8b (155 mg) in dichloromethane/methanol v/v 2:1 (9 mL). The mixture was cooled at 0° C. under argon atmosphere and trichloroisocyanuric acid (ALDRICH, 40 mg) was added. The solution was stirred under nitrogen atmosphere at 0° C. for 55 minutes, filtered and washed with dichloromethane/methanol v/v 2:1 (13 mL). The filtrate was evaporated to dryness, 10% sodium carbonate was added and the mixture was stirred. The solid was filtered and washed with 10% Na₂CO₃ (2×) and acetonitrile (6 mL), dried under vacuum to give 130 mg of the title compound as a white solid. ¹H-NMR (δ, ppm, DMSO-d₆): 11.50(bd, 1H); 7.64(t, 1H); 7.50(d, 1H); 7.34-7.32(m, 2H); 7.26(d, 2H); 7.08(d, 2H); 5.59(bd, 1H); 4.243(s, 2H); 2.45(s, 3H).

Example 3

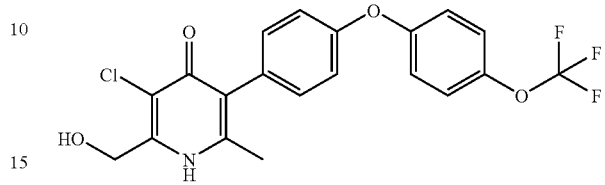

3-chloro-2-(hydroxymethyl)-6-methyl-5-[4-({4-[(trifluoromethyl)oxy]phenyl}oxy)phenyl]-4(1H)-pyridinone To a solution of Intermediate 13a (80 mg) in dichloromethane/methanol v/v 2:1 (5 mL) was added at 0° C. under nitrogen trichloroisocyanuric acid (ALDRICH, 19.5 mg). The solution was stirred under nitrogen atmosphere at 0° C. for 2 h, filtered and washed with dichloromethane/methanol v/v 2:1 (60 mL). The filtrate was evaporated to dryness and purified by chromatography (3, 5 and 10% MeOH/CH₂Cl₂) to afford 55.1 mg of the title compound as a white solid.

¹H-NMR(δ, ppm, DMSO-d₆): 11.30(bd, 1H); 7.40(d, 2H); 7.21(d, 2H); 7.14(d, 2H); 7.04(d, 2H); 5.89(bd, 1H); 4.58(s, 2H); 2.16(s, 3H).

Example 4

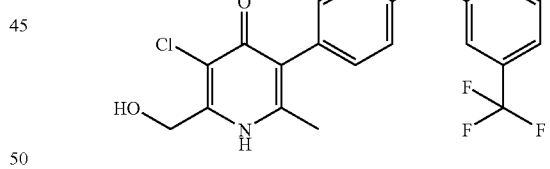

3-chloro-2-(hydroxymethyl)-6-methyl-5-(4-{[3-(trifluoromethyl)phenyl]oxy}phenyl)-4(1H)-pyridinone To a solution of intermediate 13b (214 mg) in mixture dichloromethane/methanol v/v 2:1 at 0° C., was added trichloroisocyanuric acid (53 mg). The mixture was stirred at this temperature for 40 min. The crude product was filtered, concentrated and the mixture obtained was purified by column chromatography (dichloromethane/methanol 5%). Evaporation of the solvent in the appropriate fractions gave a solid which was triturated with acetonitrile, filtered and then dried under vacuum to afford the title compound (85 mg) as a white solid.

¹H-NMR(δ, ppm, DMSO-d₆): 11.31(bs, 1H); 7.64(m, 1H); 7.50(d, 1H); 7.34(m, 2H); 7.21(d, 2H); 7.08(d, 2H); 5.89(m, 1H); 4.58 (m, 2H); 2.16(s, 3H). [ES MS] m/z 410 (MH⁺)

Example 5

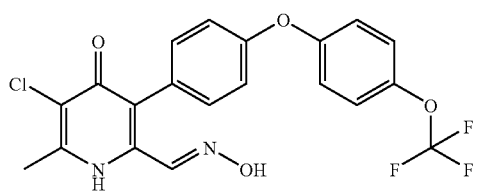

5-Chloro-6-methyl-4-oxo-3-[4-({4-[(trifluoromethyl)oxy]phenyl}oxy)phenyl]-1,4-dihydro-2-pyridinecarbaldehyde oxime Intermediate 14 (0.204 g) and hydroxylamine hydrochloride (0.167 g) were mixed in ethanol (3.37 mL) under argon atmosphere, then was added pyridine (0.167 mL) and heated at reflux (75-80° C.) for 1 hour. The reaction mixture was concentrated under vacuum to give a beige powder which was triturated with water and filtered. The solid obtained was washed with water, and then dried under vacuum to afford 0.166 g of the title compound as a white powder.

¹H NMR (δ, ppm, CD₃OD): 7.66 (s, 1H), 7.31-7.25 (m, 4H), 7.15 (d, 2H), 7.10 (d, 2H), 2.57 (s, 3H). [ES MS] m/z 439 (MH⁺).

Example 6

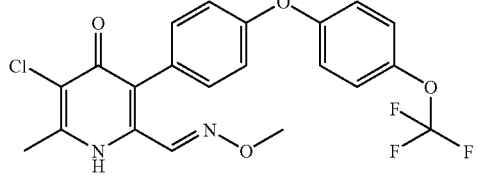

5-Chloro-6-methyl-4-oxo-3-[4-({4-[(trifluoromethyl)oxy]phenyl}oxy)phenyl]-1,4-dihydro-2-pyridinecarbaldehyde-O-methyloxime (stereochemistry unknown)

Intermediate 14 (0.100 g) and methoxylamine hydrochloride (0.079 g) were mixed in ethanol (1.65 mL) under argon atmosphere, then was added pyridine (0.079 mL) and heated at 75° C. for 2 hours. The reaction mixture was concentrated under vacuum to give syrup which was dissolved in methanol. To this solution was added a 2:1 mixture of dichloromethane/hexane. The crude product was concentrated under vacuum to give yellow solid which was filtered and washed with water, and then dried under vacuum to afford 0.088 g of the title compound as a white powder.

¹H NMR (δ, ppm, CD₃OD): 7.67 (s, 1H), 7.31-7.24 (m, 4H), 7.15-7.07 (m, 4H), 4.02 (s, 3H), 2.60 (s, 3H). [ES MS] m/z 453 (MH⁺)

Example 7

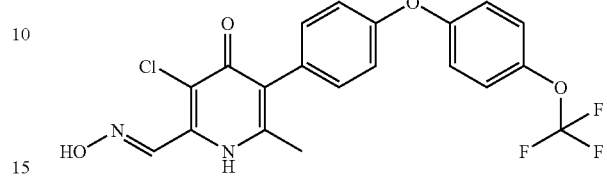

3-chloro-6-methyl-4-oxo-5-[4-({4-[(trifluoromethyl)oxy]phenyl}oxy)phenyl]-1,4-dihydro-2-pyridinecarbaldehyde oxime (stereochemistry unknown)

Intermediate 15 was dissolved under inert atmosphere in EtOH (2.8 mL). Then hydroxylamine hydrochloride (139 mg) and pyridine (0.139 mL) were added and the mixture heated under reflux for aprox 2 h. The mixture was cooled and concentrated to dryness. The resulting crude product was diluted with water and washed several times with water. The resulting solid was then triturated with acetonitrile for 2 h and then filtered, washed with acetonitrile and vacuum dried to afford the title compound (50 mg) as an off-white solid.

¹H-NMR(δ, ppm, DMSO-d₆): 12.35(s, 1H); 11.52(s, 1H); 8.32(s, 1H); 7.40(d, 2H); 7.20(d, 2H); 7.15(d, 2H); 7.05(d, 2H); 2.17(s, 3H). [ES MS] m/z 439 (MH⁺).

Example 8

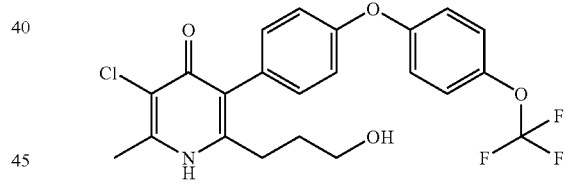

3-chloro-6-(3-hydroxypropyl)-2-methyl-5-[4-({4-[(trifluoromethyl)oxy]phenyl}oxy)phenyl]-4(1H)-pyridinone To a solution of Intermediate 16 (0.113 g) in THF (1.50 mL) at 0° C. under argon atmosphere was slowly added a 1.5 M solution of diisobutyl aluminium hydride in hexane (DIBAH, 0.89 mL). The reaction mixture was warmed to room temperature and stirred overnight. After 22 hours the mixture was quenched with water and extracted with ethyl acetate (3×20 mL). The combined organic layers were washed with brine, dried over anhydrous Na₂SO₄ and concentrated under reduced pressure to give a brown oily crude product, which was purified by column chromatography on silica gel (eluent dichloromethane/methanol, 0-5%). 0.032 g of a mixture of the title product and the partially hydrogenated 3-hydroxy-1-propenyl derivative were obtained. In order to complete the reaction, to a solution of this mixture in ethyl acetate (2.5 mL) under N₂ atmosphere was added palladium 10% w/w on activated charcoal (0.008 g) and the solution was allowed to react with 1.38×10$^5$ Pa (20 psi) of hydrogen gas for 21 hours. The catalyst was removed by filtration, washing successively with ethyl acetate (2×5 mL) and methanol (1×5 mL) and the solvents were evaporated to dryness under vacuum to give a black oil, which was purified by column chromatography on silica gel (eluent methanol/dichloromethane 0-5% and methanol/diethyl ether 0-5%). 0.013 g of the pure title product were obtained as a yellow solid.

$^1$H NMR (δ, ppm, DMSO): 7.40 (d, 2H), 7.17 (d, 2H), 7.14 (d, 2H), 7.05 (d, 2H), 3.26-3.24 (m, 2H), 2.38 (s, 5H), 1.63-1.53 (m, 2H). [ES MS] m/z 454 (MH$^+$).

Biological Assays

The compounds of this invention may be tested in one of several biological assays to determine the concentration of compound which is required to have a given pharmacological effect.

In Vitro Anti-Malarial Activity Against *Plasmodium falcinarum* IC$_{50}$ Assay/[$^3$H]-Hypoxanthine Assay I. Materials Parasite.

*Plasmodium falciparum* Strains.

Culture Medium.

The culture medium comprised RPMI 1640 with 25 mM HEPES, sodium bicarbonate and glutamine (GIBCO™ cat. ref.: 52400), supplemented with 10% of pooled human sera AB (Irvine Scientific, cat. ref.: 5009) and HT supplement (0.15 mM hypoxanthine and 24 μM thymidine), (GIBCO™ cat. ref.: 41065). Human sera were decomplemented 30 min. at 56° C., aliquoted and stored frozen at −20° C. until use in this culture medium.

This culture medium ("complete medium") was usually prepared fresh just before use and pre-warmed to 37° C.

Red Blood Cells.

Red blood cells O+ stock suspensions were prepared from whole blood bags coming from incomplete blood donation, provided by the Spanish Red Cross (<25 days after sampling). This "whole blood" was aliquoted and stored at 4° C.

To prepare red blood cells for the assay, the whole blood was centrifuged and washed 3 times with RPMI without serum. The upper phase, containing white blood cells was removed. The washed red blood cells were kept as a 50% suspension in complete medium. The prepared cells were stored at 4° C. and were employed in the assay at any time up to 4 days after preparation.

II. Compounds

Compound Preparation

Test compounds were dissolved at 2 mg/ml in 100% DMSO on the day of the assay. If necessary, complete dissolution was achieved by gentle heating (the mixture was heated at a temperature <37° C.) and sonication (sonication bath).

Before test compounds were added to the parasites, the percentage of DMSO in the compound solution was reduced by further dilutions of the solution with culture medium prepared in the same way as described above for complete medium, but which did not contain hypoxanthine. The final concentration of DMSO in the assay plates was not permitted to exceed 0.2%, so that it did not produce any detectable undesired effects on the development of the parasite. For IC$_{50}$ determinations, 10 serial 2-fold dilutions were prepared in complete medium in the presence of a constant amount of DMSO. Any obvious signs of insolubility of the stock solutions in 100% DMSO or precipitation when these solutions were diluted in assay media, were recorded.

III. *Plasmodium falciparum* Culture (Parasite)

*Plasmodium falciparum* strains were maintained in complete medium at an hematocrit of 5% in continuous culture using a method adapted from that published by Trager and Jensen(1) and Traeger(2).

The parasitemia was calculated by counting the percentage of parasitized erythrocytes by optical microscopy. Thin films of blood were made every day from each culture flask, fixed with methanol and stained for 10 min. in Giemsa (Merck, cat. ref.: 1.09204) at 10% in buffered water pH 7.2. The glass slides were observed and counted with an optical microscope (Nikon, Eclipse E200) equipped with a 100× immersion oil objective.

The culture was maintained at an hematocrit of 5%, with a daily change of medium and was diluted when parasitemia had reached about 5%. The parasite population was asynchronous, composed of a stable proportion (≅70%) of young trophozoites (ring forms) and showed a regular rate of growth of 3 to 3.5 times the initial number of parasites daily.

Growth was achieved in culture flasks (canted neck, Corning) incubated at 37° C. under low oxygen atmosphere (5% $CO_2$, 5% $O_2$, 95% $N_2$).

IV. IC$_{50}$ Assay

[$^3$H] Hypoxanthine incorporation assay was conducted using a method adapted from Desjardins et al. (3). The assays were performed in 96 wells flat bottom microplates.

1. Serial dilutions of the test compounds (50 μl of a 5× solution/well) were deposited in duplicate. Compounds of the invention were tested in this assay. Chloroquine and Atovaquone were used as control compounds for each assay.
2. The inoculum was prepared as a suspension of parasitized red blood cells (PRBCs) at 2.5% of hematocrit and 0.5% of parasitemia in culture medium prepared in the same way as described above for complete medium, but which did not contain hypoxanthine.
3. [$^3$H]-Hypoxanthine (Amersham Biosciences, cat. ref.: TRK74) was added extemporaneously to the inoculum suspension at a concentration of 1 μCi/ml (equating to 0.25 μCi/well). 200 μl of the resulting suspension was distributed into each well (other than the control well H12 described below) leading to a final volume of 250 μl per well, at 2% of hematocrit and 0.5% of parasitemia/well.
4. In each plate, 2 columns were reserved for control wells:
   Column 11: Positive control wells: PRBCs with 0.2% DMSO—(i) to determine DMSO solvent effect on parasite growth (at a final concentration of 0.2%) and (ii) to compare with cultures treated with test compounds.
   Column 12 (comprising wells A12-H12):
   A12-D12—Background value wells: Uninfected RBCs—blank control to obtain the background reading from RBCs without parasites.
   E12-G12—Solvent effect wells: PRBCs without DMSO—to determine DMSO solvent effect on PRBCs by comparing these wells with column 11 wells.
   H12-Non-radioactive well: PRBCs with cold hypoxanthine—(i) to carry out a thin blood film to determine parasitemia value after incubation by microscopy and (ii) to ensure that the parasites have grown properly during the assay. (200 μl of inoculum suspension was prepared as described above (Items 2 and 3) but with non-tritiated hypoxanthine instead of [³H]-hypoxanthine, then added to this well to a final volume of 250 µl).

5. The plates were incubated for 48 hours at 37° C. under low oxygen atmosphere. At the end of the assay, a thin film was made with the non-radioactive sample (well H12) for a visual control of the development of the parasites. Incorporation was stopped by freezing the plates overnight at −80° C.

6. The growth was quantified by measuring the level of incorporation of [³H]-hypoxanthine into the nucleic acids of the parasite. After thawing the plates, the content of the wells was harvested on glass fibre filters (Wallac, cat. ref.: 1450-421) with a semi-automated cell-harvester (Harvester 96, TOMTEC). The filters were dried and treated with a Melt-on scintillator (Meltilex® A, PerkinElmer cat. ref.: 1450-441). Incorporation of radioactivity was measured with a β-counter (Wallac Microbeta, PerkinElmer).

The assays were repeated at least three independent times.

V. Analysis of the Data

The value of each well was corrected by subtracting the background value from the absolute value. Background was calculated for each plate as the average value in cpm of the uninfected control wells.

For each concentration of a given test compound, the average (mean) value of the duplicate samples was calculated.

For each concentration of each test compound, the percentage of inhibition was then calculated by comparison with the value obtained from a control well containing PRBCs which was diluted with DMSO to achieve the same well volume but in the absence of test compound. The control well used here is the column 11 well described above (taking a mean value over all column 11 wells).

Analysis of the data were performed using Excel and GraphPad Prism 3.0 software. Results were expressed as the average±standard deviation of at least 3 independent experiments performed on different days.

VI. Bibliography

1. Trager W, Jensen J B. Human malaria parasites in continuous culture. Science. 1976 August 20;193(4254):673-5.
2. Trager W. Cultivation of malaria parasites. Methods Cell Biol. 1994;45:7-26.
3. Desjardins R E, Canfield C J, Haynes J D, Chulay J D. Quantitative assessment of antimalarial activity in vitro by a semiautomated microdilution technique. Antimicrob Agents Chemother 1979 Dec.;16(6):710-8.

Compound Solubility Determination

I. Materials

Compounds

An amount of 3 mg solid compound with LC-MS purity ≧95% was required. This amount was split between 3 different glass vials (1.8 ml volume each), placing 1 mg compound into each one.

Solvents and buffers

Organic solvents of HPLC grade were used. Ultra pure water (Milli-Q grade) was used. Buffers were prepared with ultra pure water and filtered using 0.45µ nylon filters. The compositions of each solvent employed in this assay are described below (part III).

II. Procedures

1. Procedure for Gross Solubility Determination:
   a) 100 µl of solvent was added to each vial with a digital pipette (Eppendorf Research pro).
   b) The mixture was subsequently subjected to vortexing for 1 min and sonicated for 5 minutes.
   c) Steps a) and b) were repeated until a final volume of 1 ml was reached in each vial.
   d) A microscope was used to examine the sample in each vial.
   e) The solubility of the compound in each sample was calculated as < the final concentration after all of the sample has dissolved and > the concentration before the last solvent addition.
   f) The solubility of the compound was calculated to be the mean value of the three vial samples.

2. Determination of Equilibrium Solubility (Assuming Chemical Stability in the Desired Solvent is Not a Problem).

For each of the three vial samples prepared as described above, in which the amount of compound was totally dissolved, the following procedure was subsequently carried out:
   a) A small amount (approx. 0.1 mg) of additional solid compound was added to the vial to maintain an excess of the compound in the mixture in the form of undissolved solid.
   b) The samples were magnetically stirred for 24 hr. If required, additional solid compound (0.1 mg) was added to maintain excess of it and then the samples were stirred again.
   c) Then the samples were filtered (Millipore Milex filters nylon 0.2 um) and three aliquots were taken (one from each of the three vials) and analysed by LC-MS.
   d) The pH of the final solution in each sample was measured with a pH-meter (WTW pH330i and a pH-electrode Sentix 41).

3. LC-MS Assay for Analytical Quantification

All filtered aliquots were analysed by LC-MS. The analysis was carried out with a Luna 5 µC18(2) column 4.6×150 mm, using a HP1100HPLC instrument interfaced with a Waters ZMD-2000 MS spectrometer. The concentration of the final sample as prepared above was calculated from that of a reference calibration curve obtained from serial dilutions of a 2 mM solution of the compound under investigation in DMSO (Aldrich cat. ref.: 27685-5) stock solution.

4. Analysis of Data

The analysis of all LC-MS data was performed with MassLynx 3.4 software. Statistical and graphic analysis of data was performed using Microsoft Excel. The concentration (µM) and solubility (µg/ml) for each compound was calculated using the peak areas from the sample and those from the calibration curve.

III. Compositions of Solvents Used in These Assays

A) FaSSIF is a solvent which simulates the Fasted State of the Intestinal Fluid. (FaSSIF: Fasted State Simulated Intestinal Fluid). Its composition is as given in the table below.

| Composition of FaSSIF and the pH 6.8 buffer used in FaSSIF | | |
|---|---|---|
| Composition of FaSSIF | | |
| | Conc. | Quantity per 100 ml |
| NaTaurochol. | 5 mM | 269 mg |
| Lecithin | 1.5 mM | 114 mg |
| pH 6.8 Buffer | Qs | Qs 100 ml |

-continued

Composition of FaSSIF and the pH 6.8 buffer used in FaSSIF

Composition of pH 6.8 Buffer

| | Conc. | Quantity per L |
|---|---|---|
| $KH_2PO_4$ | 0.029 M | 3.947 g |
| KCl | 0.22 M | 16.401 g |
| NaOH | Qs pH 6.8 | |
| Water | N/A | Qs 1 L |

FaSSIF Preparation Procedure.

1. Preparation of 1 L of pH 6.8 Buffer Solution
1.a. 3.947 g potassium phosphate and 16.401 g potassium chloride were dissolved in approx. 900 ml of water.
1.b. The pH was adjusted to 6.8 by slow addition of 0.1 N sodium hydroxide (Scharlau SO 0441010C) under magnetic stirring.
1.c The mixture was diluted to a volume of 1000 ml with water.
2. Preparation of 100 ml of FaSSIF
2.a. 269 mg NaTaurochol. (Aldrich T-4009) was dissolved in approx. 80 ml of pH 6.8 buffer.
2.b. 114 mg lecithin (Sigma P-7318) was dissolved in this NaTaurochol/buffer solution (this was carried out with a nitrogen filled glove bag).
2.c. The resulting mixture was diluted to a volume of 100 ml with further pH 6.8 buffer
2.d. The final solution was covered with a layer of nitrogen or alternative inert gas. The bottle was sealed with parafilm and stored at 4° C.
B) FeSSIF is a solvent which simulates the Fed State of the Intestinal Fluid. (FeSSIF: Fed State Simulated Intestinal Fluid). Its composition is as given in the table below.

Composition of FeSSIF and the pH 5.0 buffer used in FeSSIF

Composition of FeSSIF

| | Conc. | Quantity per 100 ml |
|---|---|---|
| NaTaurochol. | 15 mM | 806.5 mg |
| Lecithin | 3.8 mM | 288 mg |
| pH 5.0 Buffer | Qs | Qs 100 ml |

-continued

Composition of FeSSIF and the pH 5.0 buffer used in FeSSIF

Composition of pH 5.0 Buffer

| | Conc. | Quantity per L |
|---|---|---|
| Glacial Acetic acid | 0.137 M | 8.250 ml |
| KCl | 0.20 M | 15.2 g |
| NaOH | Qs pH 5.0 | |
| Water | N/A | Qs 1 L |

Reference(s): Galia, Nicolaides, Horter, Lobenberg, Reppas, and Dressman - Pharmaceutical Research, Vol. 15, No. 5, 1998

FeSSIF Preparation Procedure.

1. Prepare 1 L of pH 5 Buffer Solution
1.a. 15.2 g potassium chloride and 8.25 ml glacial acetic acid were dissolved in approx. 900 ml of water.
1.b. The pH was adjusted to 5 by slow addition of NaOH 0.1N (Scharlau SO 0441010C) under magnetic stirring.
1.c The mixture was diluted to a volume of 1000 ml with water.
2. Preparation of 100 mL of FeSSIF
2.a. 806.5 mg NaTaurochol (Aldrich T-4009) was dissolved in 80 ml of pH 5 buffer.
2.b. 288 mg lecithin (Sigma P-7318) was dissolved in this NaTaurochol/buffer solution (carried out with a nitrogen filled glove bag).
2.c. The resulting solution was diluted to a volume of 100 ml with pH 5 buffer.
2.d. The final solution was covered with a layer of nitrogen or alternative inert gas. The bottle was sealed with parafilm and stored at 4° C.
C) Solubility at pH 7.4 was determined in phosphate buffered saline (PBS) (Fluka cat. ref.: 79383)
D) Solubility at pH 1.0 was determined in 0.1 N HCl solution (Scharlau AL0744010C)
E) Solubility at pH 4.5 was determined in sodium citrate 0.5M solution. (Aldrich 25,127-5)

Results of in Vitro Activity Assay and Solubility Determination Assays

In Vitro Assay

All Examples of the present invention (Examples 1-8) described hereinabove were found to have an $IC_{50}$ value of less than 75 ng/ml.

Solubility Determination Assays

The solubility of all Examples of the present invention (Examples 1-8) was tested in each of the two solvents FaSSIF and FeSSIF. The data are shown in the table below.

Solubility Table

| Structure | Example | Solubility in FaSSIF μg/ml | Solubility in FeSSIF μg/ml |
|---|---|---|---|
| (structure shown) | 1 | ** | *** |

-continued
Solubility Table
| Structure | Example | Solubility in FaSSIF μg/ml | Solubility in FeSSIF μg/ml |
|---|---|---|---|
| 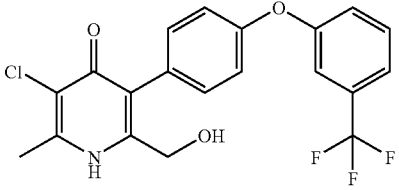 | 2 |  |  |
| 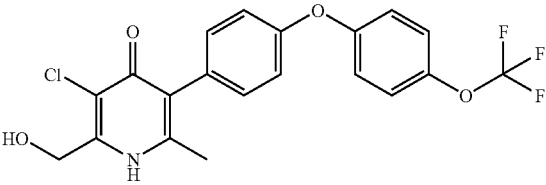 | 3 | * | ** |
| 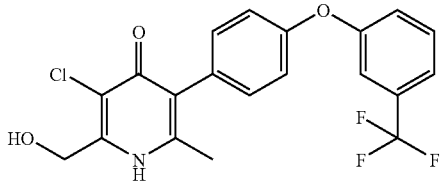 | 4 |  | ** |
| 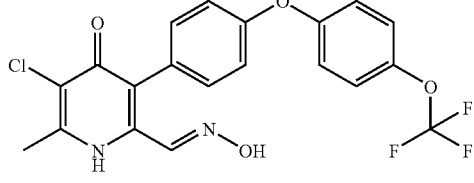 | 5 | * | ** |
| 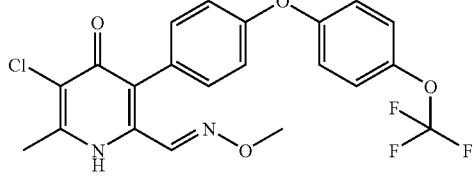 | 6 | * | ** |
| 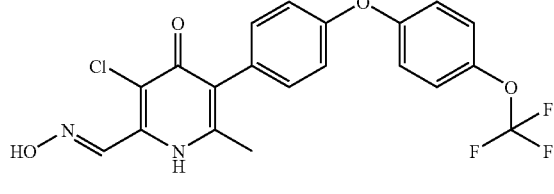 | 7 |  | * |
| 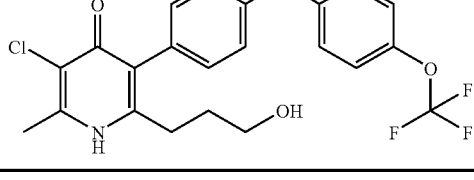 | 8 | ** | ** |
Key to Table
S = solubility in μg/ml
S < 1 *
1 < S < 5 **
5 < S < 10 ***
10 < S < 50 ****

The invention claimed is:

1. A compound which is 3-chloro-6-(hydroxymethyl)-2-methyl-5-[4-({4-[(trifluoromethyl)oxy]phenyl}oxy)phenyl]-4(1H)-pyridinone or a pharmaceutically acceptable salt thereof.

2. A composition comprising the compound of claim 1 or a pharmaceutically acceptable salt thereof and one or more pharmaceutically acceptable carriers and/or excipients.

3. A method for the treatment of a patient suffering from malaria comprising administrating to the patient an effective amount of the compound of claim 1 or a pharmaceutically acceptable salt thereof.

4. A process comprising the step of chlorinating 2-(hydroxymethyl)-6-methyl-3-[4-({4-[(trifluoromethyl)oxy]phenyl}oxy)phenyl]-4(1H)-pyridinone under conditions sufficient to form the compound of claim 1.

5. The process of claim 4 wherein the 2-(hydroxymethyl)-6-methyl-3-[4-({4-[(trifluoromethyl)oxy]phenyl}oxy)phenyl]-4(1H)-pyridinone is prepared by reductive opening and cyclization of 1-{3-(hydroxymethyl)-4-[4-({4-[(trifluoromethyl)oxy]phenyl}oxy)phenyl]-5-isoxazolyl}-2-propanone.

6. The process of claim 5 wherein the reductive opening and cyclization is carried out using palladium on activated charcoal, or hexacarbonylmolybdenum in a suitable solvent.

7. The process of claim 5 wherein the 1-{3-(hydroxymethyl)-4-[4-({4-[(trifluoromethyl)oxy]phenyl}oxy)phenyl]-5-isoxazolyl}-2-propanone is prepared by acylation of {5-methyl-4-[4-({4-[(trifluoromethyl)oxy]phenyl}oxy)phenyl]-3-isoxazolyl}methanol.

8. A process for preparing the compound of claim 1 comprising the steps of:
 a) acylating {5-methyl-4-[4-({4-[(trifluoromethyl)oxy]phenyl}oxy)phenyl]-3-isoxazolyl}methanol under such conditions to form 1-{3-(hydroxymethyl)-4-[4-({4-[(trifluoromethyl)oxy]phenyl}oxy)phenyl]-5-isoxazolyl}-2-propanone;
 b) reductively opening and cyclizing the 1-{3-(hydroxymethyl)-4-[4-({4-[(trifluoromethyl)oxy]phenyl}oxy)phenyl]-5-isoxazolyl}-2-propanone under such conditions to form 2-(hydroxymethyl)-6-methyl-3-[4-({4-[(trifluoromethyl)oxy]phenyl}oxy)phenyl]-4(1H)-pyridinone; and
 c) chlorinating the 2-(hydroxymethyl)-6-methyl-3-[4-({4-[(trifluoromethyl)oxy]phenyl}oxy)phenyl]-4(1H)-pyridinone under such conditions to form the compound of claim 1.

9. A compound which is 3-chloro-6-(hydroxymethyl)-2-methyl-5-[4-({44[(trifluoromethyl)oxy]phenyl}oxy)phenyl]-4(1H)-pyridinone.

10. A composition comprising the compound of claim 9 and one or more pharmaceutically acceptable carriers and/or excipients.

* * * * *